US009526865B2

(12) United States Patent
Quick

(10) Patent No.: US 9,526,865 B2
(45) Date of Patent: *Dec. 27, 2016

(54) RETRACTION AND ASPIRATION DEVICE FOR TREATING EMBOLISM AND ASSOCIATED SYSTEMS AND METHODS

(71) Applicant: Inceptus Medical, LLC, Aliso Viejo, CA (US)

(72) Inventor: Richard Quick, Mission Viejo, CA (US)

(73) Assignee: Inceptus Medical, LLC, Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/834,793

(22) Filed: Aug. 25, 2015

(65) Prior Publication Data

US 2015/0360001 A1 Dec. 17, 2015

Related U.S. Application Data

(63) Continuation of application No. 14/735,110, filed on Jun. 9, 2015.

(Continued)

(51) Int. Cl.
*A61B 17/221* (2006.01)
*A61M 25/01* (2006.01)
(Continued)

(52) U.S. Cl.
CPC ........ *A61M 25/0122* (2013.01); *A61B 17/221* (2013.01); *A61F 2/95* (2013.01);
(Continued)

(58) Field of Classification Search
CPC . A61B 17/22; A61B 17/22031; A61B 17/221; A61B 17/32056; A61B 2017/22034; A61B 2017/22035; A61B 2017/22038; A61B 2017/22072; A61B 2017/22075; A61B 2017/22078; A61B 2017/22079; A61B 2017/2212; A61B 2017/2215; A61B 2017/2217; A61B 2217/005; A61F 2002/9517; A61F 2002/9528; A61F 2002/9534; A61M 25/0122; A61M 25/0136; A61M 2025/09116

See application file for complete search history.

(56) References Cited

U.S. PATENT DOCUMENTS 3,435,826 A 4/1969 Fogarty
3,923,065 A 12/1975 Nozick et al.
(Continued)

FOREIGN PATENT DOCUMENTS

JP 6190049 7/1994
JP 2004097807 4/2004
(Continued)

OTHER PUBLICATIONS

Final Office Action in U.S. Appl. No. 14/299,933, mailed Dec. 29, 2014, 15 pages.
(Continued)

*Primary Examiner* — Ryan J Severson
(74) *Attorney, Agent, or Firm* — Perkins Coie LLP

(57) ABSTRACT

Retraction and aspiration devices, systems, and methods are disclosed herein. One aspect of the present technology, for example, is directed toward an apparatus for use with a catheter system configured to enable intravascular delivery of an interventional device to a treatment site in a blood vessel. The apparatus can include a housing configured to be releasably coupled to a proximal portion of the catheter system and an actuation mechanism coupled to the housing. The actuation mechanism can include a lever movably coupled to the housing, a locking portion configured to
(Continued)

engage a portion of the catheter system, and a pressure source coupled to the housing and the actuation mechanism. Movement of the lever simultaneously activates the pressure source to generate pressure, and moves the locking portion to engage and retract at least a portion of the catheter system.

30 Claims, 22 Drawing Sheets

Related U.S. Application Data

(60) Provisional application No. 62/009,805, filed on Jun. 9, 2014.

(51) Int. Cl.
*A61M 25/00* (2006.01)
*A61F 2/95* (2013.01)
*A61B 17/22* (2006.01)
*A61B 17/00* (2006.01)

(52) U.S. Cl.
CPC .... *A61M 25/0082* (2013.01); *A61M 25/0113* (2013.01); *A61B 2017/00557* (2013.01); *A61B 2017/2212* (2013.01); *A61B 2017/2215* (2013.01); *A61B 2017/22034* (2013.01); *A61B 2017/22079* (2013.01); *A61B 2017/22094* (2013.01); *A61B 2217/005* (2013.01); *A61F 2002/9528* (2013.01); *A61M 2210/0693* (2013.01); *A61M 2210/12* (2013.01)

(56) References Cited

U.S. PATENT DOCUMENTS

| | | |
|---|---|---|
| 4,030,503 A | 6/1977 | Clark, III |
| 4,650,466 A | 3/1987 | Luther |
| 4,873,978 A | 10/1989 | Ginsburg |
| 4,883,458 A | 11/1989 | Shiber |
| 4,890,611 A | 1/1990 | Monfort et al. |
| 5,011,488 A | 4/1991 | Ginsburg |
| 5,059,178 A | 10/1991 | Ya |
| 5,102,415 A | 4/1992 | Guenther et al. |
| 5,129,910 A | 7/1992 | Phan et al. |
| 5,192,286 A | 3/1993 | Phan et al. |
| 5,192,290 A | 3/1993 | Hilal |
| 5,370,653 A | 12/1994 | Cragg |
| 5,476,450 A | 12/1995 | Ruggio |
| 5,490,859 A | 2/1996 | Mische et al. |
| 5,746,758 A | 5/1998 | Nordgren et al. |
| 5,749,858 A | 5/1998 | Cramer |
| 5,766,191 A | 6/1998 | Trerotola |
| 5,827,304 A | 10/1998 | Hart |
| 5,868,708 A | 2/1999 | Hart et al. |
| 5,873,882 A | 2/1999 | Straub et al. |
| 5,876,414 A | 3/1999 | Straub |
| 5,882,329 A | 3/1999 | Patterson et al. |
| 5,972,019 A | 10/1999 | Engelson et al. |
| 6,066,149 A | 5/2000 | Samson et al. |
| 6,221,006 B1 | 4/2001 | Dubrul et al. |
| 6,238,412 B1 | 5/2001 | Dubrul et al. |
| 6,254,571 B1 | 7/2001 | Hart |
| 6,306,163 B1 | 10/2001 | Fitz |
| 6,368,339 B1 | 4/2002 | Amplatz |
| 6,383,205 B1 | 5/2002 | Samson et al. |
| 6,454,741 B1 | 9/2002 | Muni et al. |
| 6,454,775 B1 | 9/2002 | Demarais et al. |
| 6,458,139 B1 | 10/2002 | Palmer et al. |
| 6,511,492 B1 | 1/2003 | Rosenbluth et al. |
| 6,514,273 B1 | 2/2003 | Voss et al. |
| 6,544,279 B1 | 4/2003 | Hopkins et al. |
| 6,605,074 B2 | 8/2003 | Zadno-Azizi et al. |
| 6,605,102 B1 | 8/2003 | Mazzocchi et al. |
| 6,635,070 B2 | 10/2003 | Leeflang et al. |
| 6,645,222 B1 | 11/2003 | Parodi et al. |
| 6,660,013 B2 | 12/2003 | Rabiner et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,767,353 B1 | 7/2004 | Shiber |
| 7,004,954 B1 | 2/2006 | Voss et al. |
| 7,036,707 B2 | 5/2006 | Aota et al. |
| 7,041,084 B2 | 5/2006 | Fojtik et al. |
| 7,052,500 B2 | 5/2006 | Bashiri et al. |
| 7,056,328 B2 | 6/2006 | Arnott |
| 7,179,273 B1 | 2/2007 | Palmer et al. |
| 7,220,269 B1 | 5/2007 | Ansel et al. |
| 7,244,243 B2 | 7/2007 | Lary |
| 7,285,126 B2 | 10/2007 | Sepetka et al. |
| 7,320,698 B2 | 1/2008 | Eskuri |
| 7,534,234 B2 | 5/2009 | Fojtik et al. |
| 7,578,830 B2 | 8/2009 | Kusleika et al. |
| 7,621,870 B2 | 11/2009 | Berrada et al. |
| 7,674,247 B2 | 3/2010 | Fojtik et al. |
| 7,905,896 B2 | 3/2011 | Straub |
| 7,938,820 B2 | 5/2011 | Webster et al. |
| 7,976,511 B2 | 7/2011 | Fojtik et al. |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,100,935 B2 | 1/2012 | Rosenbluth et al. |
| 8,118,829 B2 | 2/2012 | Carrison et al. |
| 8,246,641 B2 | 8/2012 | Osborne et al. |
| 8,317,748 B2 | 11/2012 | Fiorella et al. |
| 8,337,450 B2 | 12/2012 | Fojtik et al. |
| 8,491,539 B2 | 7/2013 | Fojtik et al. |
| 8,568,432 B2 | 10/2013 | Straub |
| 8,784,434 B2 | 7/2014 | Rosenbluth et al. |
| 8,845,621 B2 | 9/2014 | Fojtik et al. |
| 8,852,205 B2 | 10/2014 | Brady et al. |
| 8,932,319 B2 | 1/2015 | Martin et al. |
| 8,968,330 B2 | 3/2015 | Rosenbluth et al. |
| 9,259,237 B2 | 2/2016 | Quick et al. |
| 9,408,620 B2 | 8/2016 | Rosenbluth et al. |
| 2002/0120277 A1* | 8/2002 | Hauschild ............ A61B 17/221 606/108 |
| 2002/0147458 A1 | 10/2002 | Hiblar et al. |
| 2002/0156457 A1 | 10/2002 | Fisher |
| 2003/0028182 A1* | 2/2003 | Abboud ................ A61B 18/02 606/21 |
| 2003/0114875 A1 | 6/2003 | Sjostrom |
| 2003/0125663 A1* | 7/2003 | Coleman ........... A61M 25/0136 604/95.04 |
| 2003/0135230 A1* | 7/2003 | Massey ................ A61B 1/12 606/190 |
| 2004/0073243 A1 | 4/2004 | Sepetka et al. |
| 2005/0119668 A1 | 6/2005 | Teague et al. |
| 2006/0047286 A1 | 3/2006 | West |
| 2006/0100662 A1 | 5/2006 | Daniel et al. |
| 2006/0253145 A1 | 11/2006 | Lucas |
| 2006/0282111 A1 | 12/2006 | Morsi |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0255252 A1 | 11/2007 | Mehta |
| 2008/0015541 A1 | 1/2008 | Rosenbluth et al. |
| 2008/0167678 A1 | 7/2008 | Morsi |
| 2008/0228209 A1 | 9/2008 | DeMello et al. |
| 2008/0269798 A1 | 10/2008 | Ramzipoor et al. |
| 2009/0054918 A1 | 2/2009 | Henson |
| 2009/0062841 A1 | 3/2009 | Amplatz et al. |
| 2009/0163846 A1 | 6/2009 | Aklog et al. |
| 2009/0182362 A1 | 7/2009 | Thompson et al. |
| 2009/0292307 A1 | 11/2009 | Razack |

(56) References Cited

U.S. PATENT DOCUMENTS

| | | |
|---|---|---|
| 2010/0114113 A1 | 5/2010 | Dubrul et al. |
| 2010/0204712 A1 | 8/2010 | Mallaby |
| 2010/0249815 A1 | 9/2010 | Jantzen et al. |
| 2010/0318178 A1 | 12/2010 | Rapaport et al. |
| 2011/0060212 A1 | 3/2011 | Slee et al. |
| 2011/0152993 A1 | 6/2011 | Marchand et al. |
| 2011/0190806 A1 | 8/2011 | Wittens |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0251629 A1 | 10/2011 | Galdonik et al. |
| 2011/0264133 A1 | 10/2011 | Hanlon et al. |
| 2012/0089216 A1 | 4/2012 | Rapaport et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0232655 A1 | 9/2012 | Lorrison et al. |
| 2012/0271231 A1 | 10/2012 | Agrawal |
| 2014/0005713 A1 | 1/2014 | Bowman |
| 2015/0018860 A1 | 1/2015 | Quick et al. |
| 2015/0196744 A1 | 7/2015 | Aboytes |
| 2015/0238207 A1 | 8/2015 | Cox et al. |
| 2015/0305756 A1 | 10/2015 | Rosenbluth et al. |
| 2015/0352325 A1 | 12/2015 | Quick |
| 2015/0360001 A1 | 12/2015 | Quick |
| 2015/0374391 A1 | 12/2015 | Quick et al. |
| 2016/0113666 A1 | 4/2016 | Quick et al. |
| 2016/0143721 A1 | 5/2016 | Rosenbluth et al. |
| 2016/0262790 A1 | 9/2016 | Rosenbluth et al. |

FOREIGN PATENT DOCUMENTS

| | | |
|---|---|---|
| JP | 2005230132 | 9/2005 |
| JP | 2005323702 | 11/2005 |
| JP | 2006094876 | 4/2006 |
| WO | WO-9717889 | 5/1997 |
| WO | WO0053120 | 9/2000 |
| WO | WO-2005046736 | 5/2005 |
| WO | WO-2006110186 | 10/2006 |
| WO | WO-2007092820 | 8/2007 |
| WO | WO-2009155571 | 12/2009 |
| WO | WO-2010010545 | 1/2010 |
| WO | WO-2010023671 | 3/2010 |
| WO | WO-2010049121 | 5/2010 |
| WO | WO-2010102307 | 9/2010 |
| WO | WO-2011054531 | 5/2011 |
| WO | WO-2012009675 | 1/2012 |
| WO | WO-2012065748 | 5/2012 |
| WO | WO-2014047650 | 3/2014 |
| WO | WO-2014081892 | 5/2014 |
| WO | WO-2015006782 | 1/2015 |
| WO | WO-2015061365 | 4/2015 |

OTHER PUBLICATIONS

Gibbs, et al., "Temporary Stent as a bail-out device during percutaneous transluminal coronary angioplasty: preliminary clinical experience." British Heart Journal, 1994, 71:372-377, Oct. 12, 1993, 6 pgs.

Goldhaber, S., "Advanced treatment strategies for acute pulmonary embolism, including thrombolysis and embolectomy." Journal of Thrombosis and Haemostasis, 2009: 7 (Suppl. 1): 322-327.

Goldhaber, S. et al. "Percutaneous Mechanical Thrombectomy for Acute Pulmonary Embolism—A Double-Edged Sword." American College of Chest Physicians, Aug. 2007: 132:2, 363-372.

Gupta, S. et al., "Acute Pulmonary Embolism Advances in Treatment." JAPI, Association of Physicians India, Mar. 2008, vol. 56, 185-191.

International Search Report and Written Opinion for International App. No. PCT/US13/61470, mailed Jan. 17, 2014, 7 pages.

International Search Report and Written Opinion for International App. No. PCT/US2014/046567, mailed Nov. 3, 2014, 13 pages.

International Search Report and Written Opinion for International App. No. PCT/US2014/061645, mailed Jan. 23, 2015, 15 pages.

International Search Report for International App. No. PCT/US13/71101, mailed Mar. 31, 2014, 4 pages.

Konstantinides, S. et al., "Pulmonary embolism hotline 2012—Recent and expected trials." Thrombosis and Haemostasis, Jan. 9, 2013:33, 43-50.

Konstantinides, S. et al., "Pulmonary embolism: risk assessment and management." European Society of Cardiology European Heart Journal, Sep. 7, 2012:33, 3014-3022.

Kucher, N. et al., "Percutaneous Catheter Thrombectomy Device for Acute Pulmonary Embolism: In Vitro and in Vivo Testing." Circulation, Sep. 2005:112:e28-e32.

Kucher, N., "Catheter Interventions in Massive Pulmonary Embolism." CardiologyRounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques." Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis." American College of Chest Physicians 2008: 134:250-254.

Kuo, W. MD, "Endovascular Therapy for Acute Pulmonary Embolism", Continuing Medical Education Society of Interventional Radiology ("CME"), Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System." Cardiovascular Interventional Radiology, 2011: 34:106-113.

Muller-Hulsbeck, S. et al. "Mechanical Thrombectomy of Major and Massive Pulmonary Embolism with Use of the Amplatz Thrombectomy Device." Investigative Radiology Jun. 2001: 36: 6: 317-322.

Non-Final Office Action in U.S. Appl. No. 13/843,742, mailed Sep. 13, 2013, 16 pages.

Non-Final Office Action in U.S. Appl. No. 14/299,933, mailed Aug. 29, 2014, 10 pages.

Notice of Allowance for U.S. Appl. No. 13/843,742, mailed Mar. 12, 2014, 13 pages.

Notice of Allowance for U.S. Appl. No. 14/288,778, mailed Dec. 23, 2014, 12 pages.

Reekers, J. et al., "Mechanical Thrombectomy for Early Treatment of Massive Pulmonary Embolism." CardioVascular and Interventional Radiology, 2003: 26:246-250.

Schmitz-Rode et al., "New Mesh Basket for Percutaneous Removal of Wall-Adherent Thrombi in Dialysis Shunts." Cardiovasc Intervent Radiol 16:7-10 1993 4 pgs.

Schmitz-Rode et al., "Temporary Pulmonary Stent Placement as Emergency Treatment of Pulmonary Embolism." Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter." JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism." The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation

(56) References Cited

OTHER PUBLICATIONS of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath." Cardiovasc Intervent Radiol27-254-258, 2004, 5 pgs.
Turk et al., "Adapt Fast study: a direct aspiration first pass technique for acute stroke thrombectomy." J NeuroIntervent Surg, vol. 6, 2014, 6 pages.
Uflacker, R., "Interventional Therapy for Pulmonary Embolism." Journal of Vascular and Interventional Radiology Feb. 2001: 12:147-164.
Verma, R., MD et al. "Evaluation of a Newly Developed Percutaneous Thrombectomy Basket Device in Sheep With Central Pulmonary Embolisms." *Investigative Radiology*, Oct. 2006, 41, 729-734.
Final Office Action for U.S. Appl. No. 14,299,933, mailed Aug. 12, 2015, 7 pages.
European Patent Application No. 13838945.7, Extended European Search Report, 9 pages, Apr. 15, 2016.
International Search Report and Written Opinion for International Application No. PCT/US2015/034987, mailed Sep. 17, 2015, 12 pages.
International Search Report for International App. No. PCT/US2015/034987, mailed Jun. 9, 2015, 12 pages.

\* cited by examiner

RETRACTION AND ASPIRATION DEVICE FOR TREATING EMBOLISM AND ASSOCIATED SYSTEMS AND METHODS

CROSS-REFERENCE TO RELATED APPLICATIONS

The present application claims the benefit of U.S. Provisional Patent Application No. 62/009,805, filed Jun. 9, 2014, titled "RETRACTION AND ASPIRATION APPARATUS FOR TREATING EMBOLISM AND ASSOCIATED SYSTEMS AND METHODS," which is incorporated herein by reference in its entirety.

TECHNICAL FIELD

The present technology relates generally to devices and methods for intravascular treatment of emboli within a blood vessel of a human patient. Many embodiments of the technology relate to an apparatus for simultaneous retraction and aspiration of an embolism and associated systems and methods.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by a clot, tissue ischemia develops. The ischemia will progress to tissue infarction if the occlusion persists. Infarction does not develop or is greatly limited if the flow of blood is reestablished rapidly. Failure to reestablish blood flow can lead to the loss of limb, angina pectoris, myocardial infarction, stroke or even death.

In the venous circulation, occlusive material can also cause serious harm. Blood clots can develop in the large veins of the legs and pelvis, a common condition known as deep venous thrombosis (DVT). DVT arises most commonly when there is a propensity for stagnated blood (e.g., long distance air travel, immobility, etc.) and clotting (e.g., cancer, recent surgery, such as orthopedic surgery, etc.). DVT causes harm by: (1) obstructing drainage of venous blood from the legs leading to swelling, ulcers, pain, and infection, and (2) serving as a reservoir for blood clots to travel to other parts of the body including the heart, lungs and across an opening between the chambers of the heart (patent foramen ovale) to the brain (stroke), abdominal organs or extremities.

In the pulmonary circulation, the undesirable material can cause harm by obstructing pulmonary arteries—a condition known as pulmonary embolism. If the obstruction is upstream, in the main or large branch pulmonary arteries, it can severely compromise total blood flow within the lungs, and therefore the entire body, and result in low blood pressure and shock. If the obstruction is downstream, in large to medium pulmonary artery branches, it can prevent a significant portion of the lung from participating in the exchange of gases to the blood resulting in low blood oxygen and buildup of blood carbon dioxide.

There are many existing techniques employed to reestablish blood flow in an occluded vessel. One common surgical technique, an embolectomy, involves incising a blood vessel and introducing a balloon-tipped device (such as the Fogarty catheter) to the location of the occlusion. The balloon is then inflated at a point beyond the clot and used to translate the obstructing material back to the point of incision. The obstructing material is then removed by the surgeon. Although such surgical techniques have been useful, exposing a patient to surgery may be traumatic and best avoided when possible. Additionally, the use of a Fogarty catheter may be problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel (e.g., typically through an introducing catheter). The balloon-tipped catheter is then advanced to the point of the occlusion and inflated in order to dilate the stenosis. Balloon angioplasty is appropriate for treating vessel stenosis, but it is generally not effective for treating acute thromboembolisms as none of the occlusive material is removed and the vessel will re-stenos after dilation. Another percutaneous technique involves placing a catheter near the clot and infusing streptokinase, urokinase or other thrombolytic agents to dissolve the clot. Unfortunately, thrombolysis typically takes hours to days to be successful. Additionally, thrombolytic agents can cause hemorrhage and in many patients the agents cannot be used at all.

Various devices exist for performing a thrombectomy or removing other foreign material. However, such devices have been found to have structures which are either highly complex, cause trauma to the treatment vessel, or lack sufficient retaining structure and thus cannot be appropriately fixed against the vessel to perform adequately. Furthermore, many of the devices have highly complex structures that lead to manufacturing and quality control difficulties as well as delivery issues when passing through tortuous or small diameter catheters. Less complex devices may allow the user to pull through the clot, particularly with inexperienced users, and such devices may not completely capture and/or collect all of the clots.

Thus, there exists a need for an improved embolic extraction device.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Specific details of several embodiments of retraction and aspiration devices, systems and associated methods in accordance with the present technology are described below with reference to FIGS. 1A-10K. Although many of the embodiments are described below with respect to devices, systems, and methods for treating a pulmonary embolism, other applications and other embodiments in addition to those described herein are within the scope of the technology (e.g., intravascular procedures for indications other than the treatment of emboli, intravascular procedures for treating cerebral embolism, etc.). Additionally, several other embodiments of the technology can have different states, components, or procedures than those described herein. Moreover, it will be appreciated that specific elements, substructures, advantages, uses, and/or other features of the embodiments described with reference to FIGS. 1A-10K can be suitably interchanged, substituted or otherwise configured with one another in accordance with additional embodiments of the present technology. Furthermore, suitable elements of the embodiments described with reference to FIGS. 1A-10K can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1A-10K.

With regard to the terms "distal" and "proximal" within this description, unless otherwise specified, the terms can reference a relative position of the portions of a retraction and aspiration apparatus and/or an associated catheter system with reference to an operator and/or a location in the vasculature. Also, as used herein, the designations "rearward," "forward," "upward," "downward," etc. are not meant to limit the referenced component to use in a specific orientation. It will be appreciated that such designations refer to the orientation of the referenced component as illustrated in the Figures; the retraction and aspiration device and system of the present technology can be used in any orientation suitable to the user.

I. Selected Embodiments of Retraction and Aspiration Devices and Methods of Use

Figure 1A:
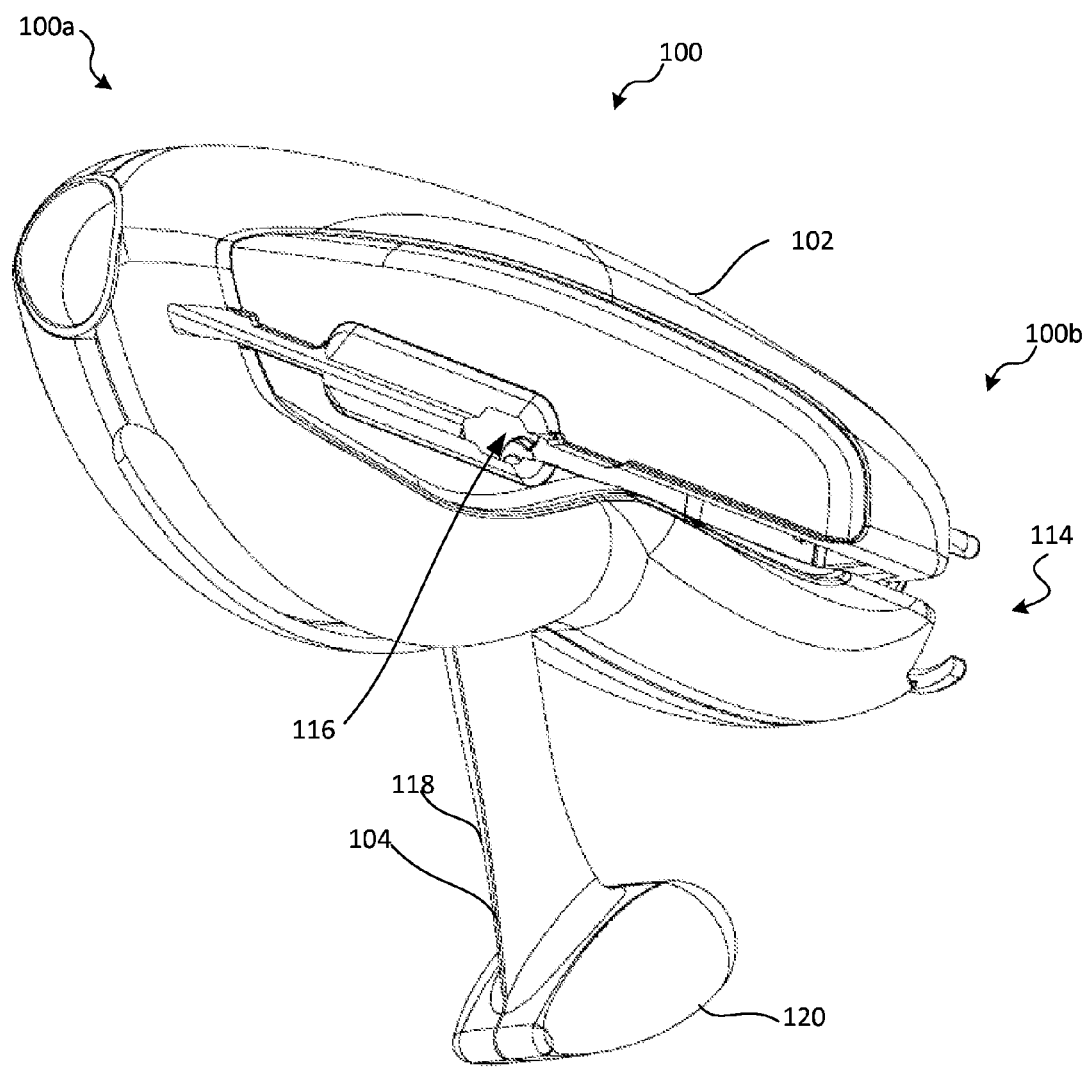
FIG. 1A is a perspective view of one embodiment of a retraction and aspiration device in accordance with the present technology shown in a first state.
Figure 1B:
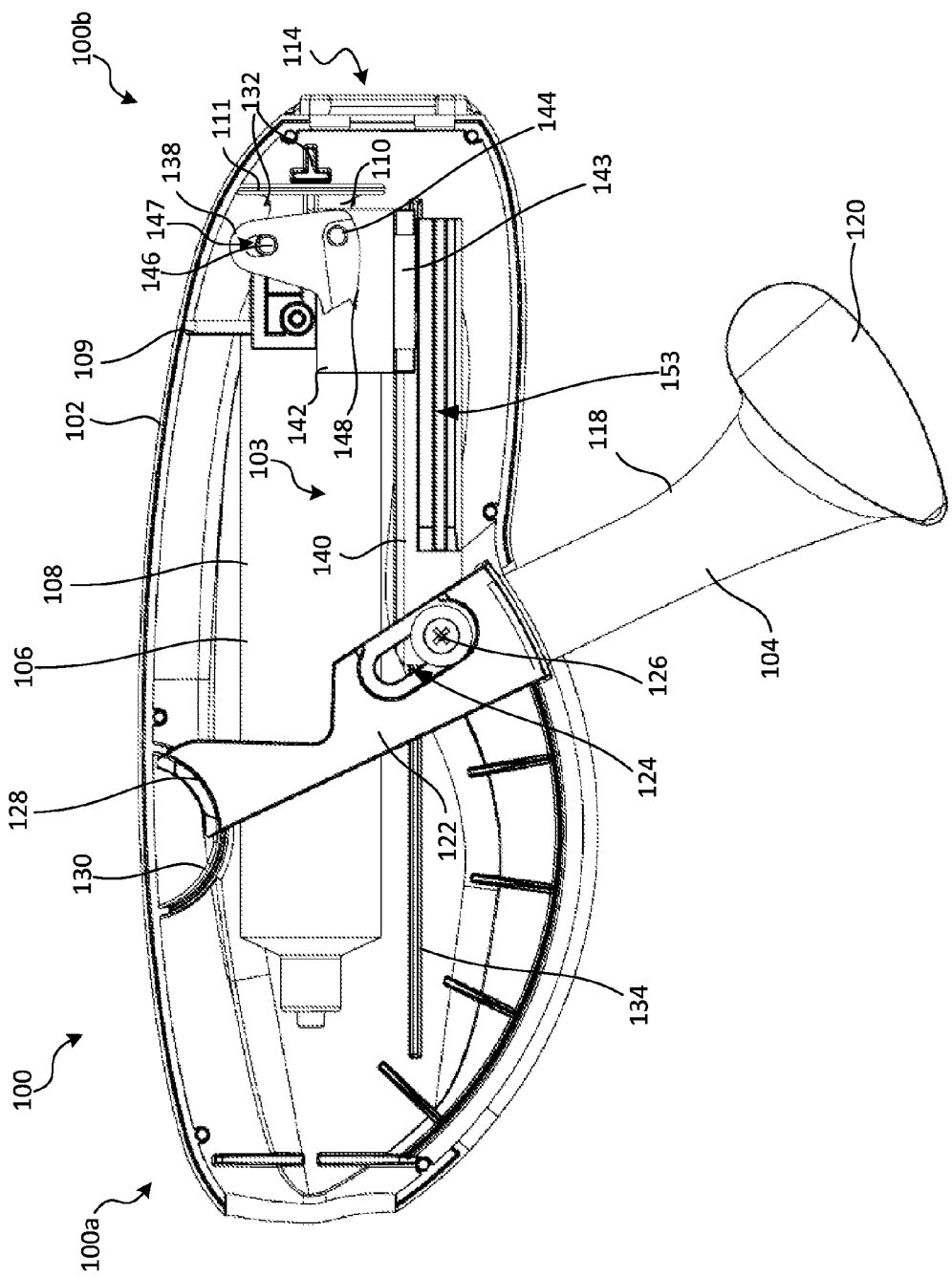
FIG. 1B is a side view of the retraction and aspiration device of FIG. 1A shown in a first state with a portion of the housing removed for purposes of illustration.

FIG. 1A is side perspective view of a retraction and aspiration device 100 (also referred to herein as the "RA device 100") configured in accordance with the present technology, shown in a first state. FIG. 1B is a side view of the RA device 100 shown in FIG. 1A with a portion of the RA device 100 removed for ease of illustration. Referring to FIGS. 1A-1B together, the RA device 100 includes a housing 102, an actuation mechanism 103 (FIG. 1B) that includes a lever 104 coupled to and extending from the housing 102, and a pressure source 106. In some embodiments the RA device 100 is configured to be coupled to the proximal portion of a catheter (not shown in FIGS. 1A-1B), such as a catheter that supports an interventional device. As described in greater detail below, when the RA device 100 is at least coupled to a catheter, movement of the lever 104 activates the actuation mechanism 103 to simultaneously generate negative pressure in the pressure source 106 and retract a portion of the catheter system.

The housing 102 can have a proximal portion 100a, a distal portion 100b, and an opening 114 at the distal portion 100b configured to receive a portion of a catheter and/or an attachment member configured to mechanically couple a catheter to the housing 102. For example, the housing 102 can include a channel 116 (FIG. 1A) that extends proximally from the opening 114 along at least a portion of the housing 102. In some embodiments, the channel 116 can extend approximately the length of the housing 102, as shown in FIG. 1A. The channel 116 can have a height at least as great as the outer diameter of the associated catheter (and/or a component of the catheter, such as a delivery sheath) such that the catheter can fit sideways through the channel 116. The housing 102 can include one or more bosses (e.g., boss 130, boss 132, and boss 134 shown in FIG. 1B) that extend into the interior of the housing 102 and are configured to guide and/or limit movement of one or more components of the RA device 100, as described in greater detail below. As shown in FIGS. 1A-1B, the housing 102 can have an undulating shape (e.g., kidney-bean shaped) to improve grip-ability of the RA device 100, for example, during movement of the lever 104. In other embodiments, the housing 102 can have other suitable shapes and/or configurations.

The pressure source 106 can be mounted at least partially within the housing 102 and configured to generate negative and/or positive pressure. For example, when the RA device 100 is coupled to a lumen of a catheter, activation of the pressure source 106 generates a negative pressure in the lumen of the catheter, as described in greater detail below with reference to FIGS. 4A-4B and 5A-5G. As shown in FIG. 1B, in some embodiments the pressure source 106 is a syringe having a barrel 108 (e.g., a 20 cc barrel), a plunger 110, and a piston (not visible) coupled to an end portion of the plunger 110. One of the plunger 110 or the barrel 108 can be fixed relative to the housing 102, while the other of the plunger 110 or the barrel 108 is moveable relative to the housing 102. For example, in the embodiment shown in FIG.

1B, the barrel 108 has an outwardly extending flange 109 coupled to a portion of the actuation mechanism 103, and the plunger 110 has an outwardly extending flange 111 coupled to the boss 132 extending from the housing 102. Accordingly, the RA device 100 is configured such that the barrel 108 can move with the actuation mechanism 103 while the plunger 110 remains generally fixed relative to the housing 102.

The pressure source 106 is moveable between a first configuration (FIGS. 1A-1B) and a second configuration (FIG. 2B) (e.g., via activation of the actuation mechanism 103, as described in greater detail below). In the first configuration, the flange 109 of the barrel 108 is closest to the flange 111 of the plunger 110. When the pressure source 106 is in the second configuration, the flange 109 of the barrel 108 is farthest from the flange 111 of the plunger 110. As the pressure source 106 moves between the first and second configurations, the pressure source 106 generates pressure. When the pressure source 106 is at rest, the pressure source 106 is not generating pressure.

Although the pressure source 106 is depicted and described herein as a syringe, the pressure source 106 can be any suitable pressure-generating device, such as an electrical pump or other mechanical pump. For example, in some embodiments the pressure source 106 can be an electrical pump controlled by an on/off switch. Moreover, although FIGS. 1A-1B show at least a portion of the pressure source 106 disposed within the housing 102, in other embodiments the pressure source 106 can be a separate component that is mechanically or electrically coupled to the RA device 100. Additionally, the RA device 100 can be coupled to more than one pressure source. In those embodiments where the pressure source is a syringe, the pressure source can be a syringe having a barrel volume between about 10 cc and about 80 cc. In some embodiments, the syringe can have a barrel volume between about 20 cc and about 40 cc (e.g., 20 cc, 30 cc, 40 cc, etc.).

Figure 2A:
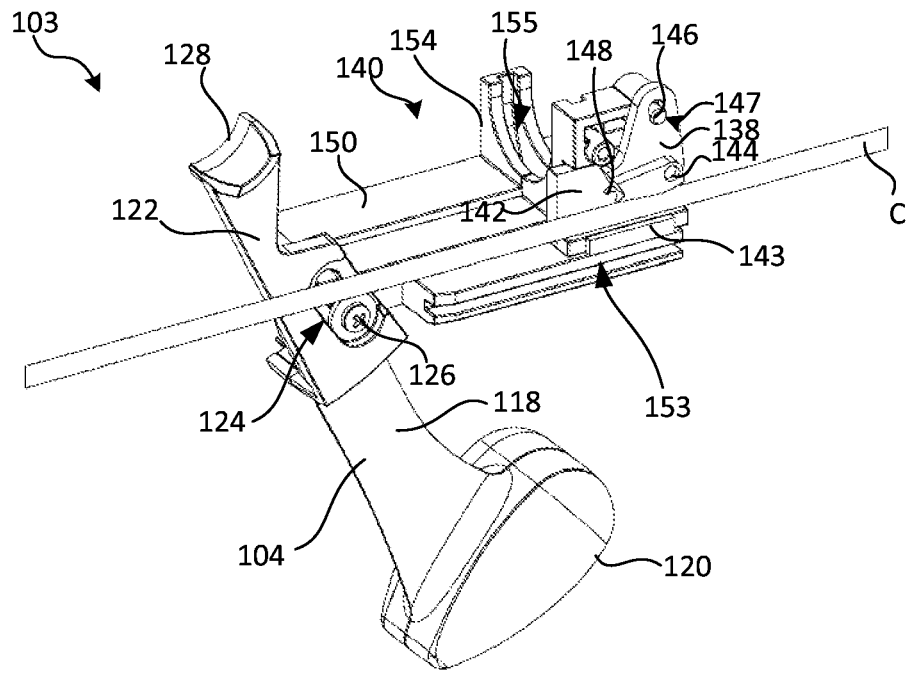
FIG. 2A is an isolated rear perspective view of the actuation mechanism of FIGS. 1A-1B shown in a first position.
Figure 2B:
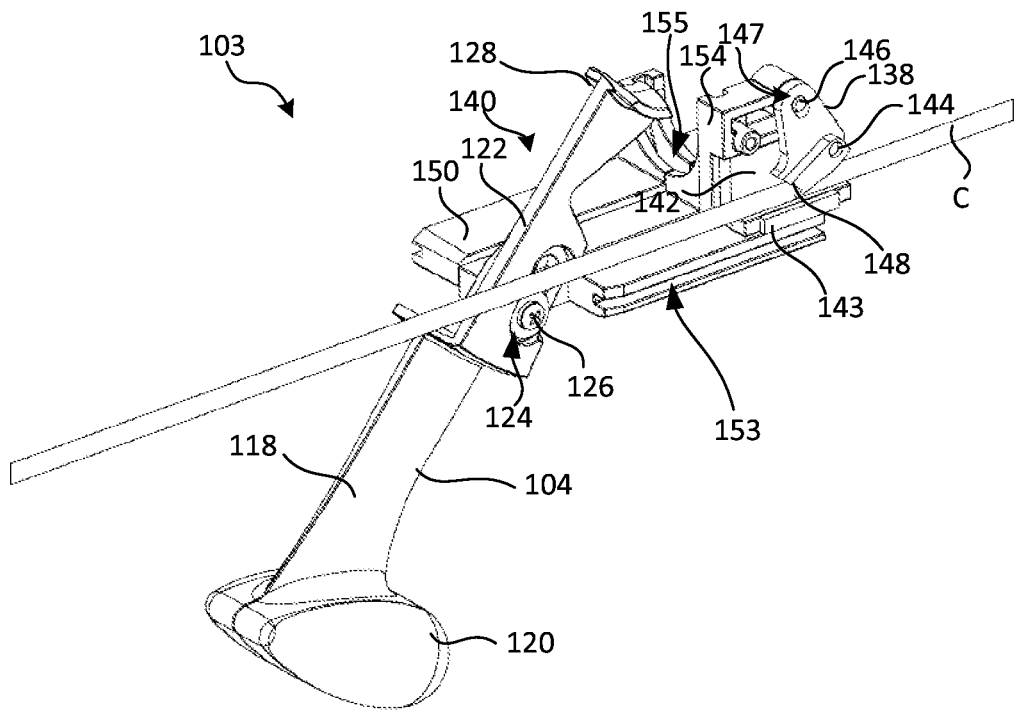
FIG. 2B is an isolated rear perspective view of the actuation mechanism of FIGS. 1A-1B shown in a second position.

FIGS. 2A and 2B are rear perspective isolated views of the actuation mechanism 103 shown in FIGS. 1A-1B in a first and second position, respectively, shown coupled to a catheter C. Referring to FIGS. 1B and 2A-2B together, the actuation mechanism 103 can include the lever 104, a first slider 140 coupled to the lever 104, a second slider 142 coupled to the first slider 140, and a cam 138 coupled to the second slider 142. The actuation mechanism 103 is configured to simultaneously activate the pressure source 106 (FIG. 1B) and interact with the catheter C in response to movement of the lever 104, as described in greater detail below.

The lever 104 can have a handle portion 118 that projects from the housing 102 and a link portion 122 disposed within the housing 102. The handle portion 118 is configured to be grasped by an operator. In some embodiments, the handle portion 118 can include an enlarged portion 120 located along the handle portion 118 furthest from the housing 102. The enlarged portion 120, for example, can be configured to increase the handle portion's surface area, thereby improving grip-ability of the handle portion 118. The link portion 122 can be configured to mechanically couple the lever 104 to the housing 102 and/or the actuation mechanism 103. For example, as shown in FIGS. 1B and 2A-2B, the link portion 122 includes a flange 128 configured to slidably engage the boss 130 of the housing 102. In some embodiments, both the flange 128 of the lever 104 and the boss 130 of the housing 102 can be curved to induce rotation of the lever 104 about the boss 130 when a user moves the handle portion 118. Accordingly, the lever 104 is moveable between a first position (FIG. 2A) and a second position (FIG. 2B). In the embodiments illustrated herein, in the first position the lever 104 is closest to the housing 102 and in the second position the lever 104 is furthest from the housing 102. In other embodiments, however, in the first position the lever 104 is furthest from the housing 102 and in the second position the lever 104 is closest to the housing 102.

The link portion 122 also includes a slot 124 that couples the lever 104 to the first slider 140 of the actuation mechanism 103 via a pin 126. The slot 124 is located along the lever 104 between the handle portion 118 and an opposite end of the lever 104. During movement of the lever 104, the pin 126 slides within and along the slot 124; as such the slot 124 pulls on the pin 126, thereby causing linear movement of the first slider 140. In sum, movement of the lever 104 between the first and second positions moves the actuation mechanism 103 between the first and second positions (and thus the RA device 100 between the first and second states).

In some embodiments, the lever 104 can be replaced by other suitable actuators, such as other suitable linear actuators (e.g., a rack-and-pinion mechanism, an electromechanical actuator, etc.). For example, in some embodiments the lever 104 can be in the form of a push button moveable between a first or off position and a second on position that simultaneously actuates the pressure source and retraction mechanism. Additionally, in some embodiments the lever 104 and/or device 100 can be configured such that pulling the lever 104 from the device 100 mechanically initiates the retraction mechanism and at the same time triggers activation of an automatic pressure source. Moreover, the lever 104 can be coupled to the housing 102 via other suitable means. For example, in some embodiments the lever 104 can be configured to pivot and/or rotate around a fixed point on the housing 102.

Referring still to FIGS. 1B and 2A-2B, the cam 138 is configured to mechanically couple the first and second sliders 140, 142. In the illustrated embodiments, the cam 138 includes a slot 147 and a locking portion 148. The cam 138 is pivotably coupled to the first slider 140, for example, via a pin 146 that extends through the slot 147. The cam 138 is fixed to the second slider 142, for example, via a pin 144. In other embodiments, the cam 138 can be coupled to the first and/or second slider 140, 142 via other suitable coupling means known in the art.

The locking portion 148 of the cam 138 is configured to engage one or more components of the associated catheter C. For example, as best shown in FIG. 2A, the locking portion 148 can include a rounded recess configured to contact the catheter C and secure the catheter C between the locking portion 148 and the second slider 142. In other embodiments, the locking portion 148 can have other suitable shapes and/or configurations. As described in greater detail below, when the actuation mechanism 103 is activated, the cam 138 rotates such that the locking portion 148 engages a portion of the catheter C, thereby securing the catheter C to a portion of the actuation mechanism 103.

The first slider 140 can include a first portion 150 and a second portion 154. The first portion 150 can be coupled to the lever 104 and configured to guide movement of the first slider 140 relative to the housing 102. In the illustrated embodiment, the first portion 150 includes a cylindrical boss (not visible) slidably received by the slot 124 positioned along the link portion 122 of the lever 104. A screw 126 is positioned within the cylindrical boss to keep the boss in the slot 124. As such, rotation of the lever 104 causes linear movement of the first slider 140. In other embodiments, the first slider 140 can be mechanically coupled to the lever by other suitable means known in the art, such as by a pin, yoke, etc. The first portion 150 also includes a slot 153 configured to receive and slide along the boss 134 (FIG. 1B) of the housing 102. The second portion 154 can be coupled to or contiguous with the first portion 150 and is configured to receive at least a portion of the pressure source 106 (FIG. 1B). The second portion 154, for example, can extend upwardly from the first portion 150 and have a semi-circular shape. The second portion 154 can include a slot 155 configured to receive the flange 109 of the barrel 108 of the pressure source 106, thereby fixing the barrel 108 relative to the first slider 140. As such, linear movement of the first slider 140 causes linear movement of the barrel 108. The second portion 156 of the first slider 140 also includes an opening (not visible) configured to receive the pin 146 extending through the slot 147 in the cam 138. As such, the first slider 140 is moveably coupled to the cam 138 via an opening in the second portion 154.

The second slider 142 is configured to receive one or more components of the catheter C. As described in greater detail below, the second slider 142 and the cam 138 together mechanically couple movement of the first slider 140 to the catheter C. In the illustrated embodiment, the second slider 142 is L-shaped and configured to receive and support a portion of the catheter C at an intersection of the L-shape. The second slider 142 can optionally include a friction pad 143 configured to engage a portion of the housing 102 to delay the movement of the second slider 142 relative to the first slider 140. Once the locking portion 148 traps the catheter C, the first slider 142 and the second slider 142 move at the same rate.

Figure 3A:
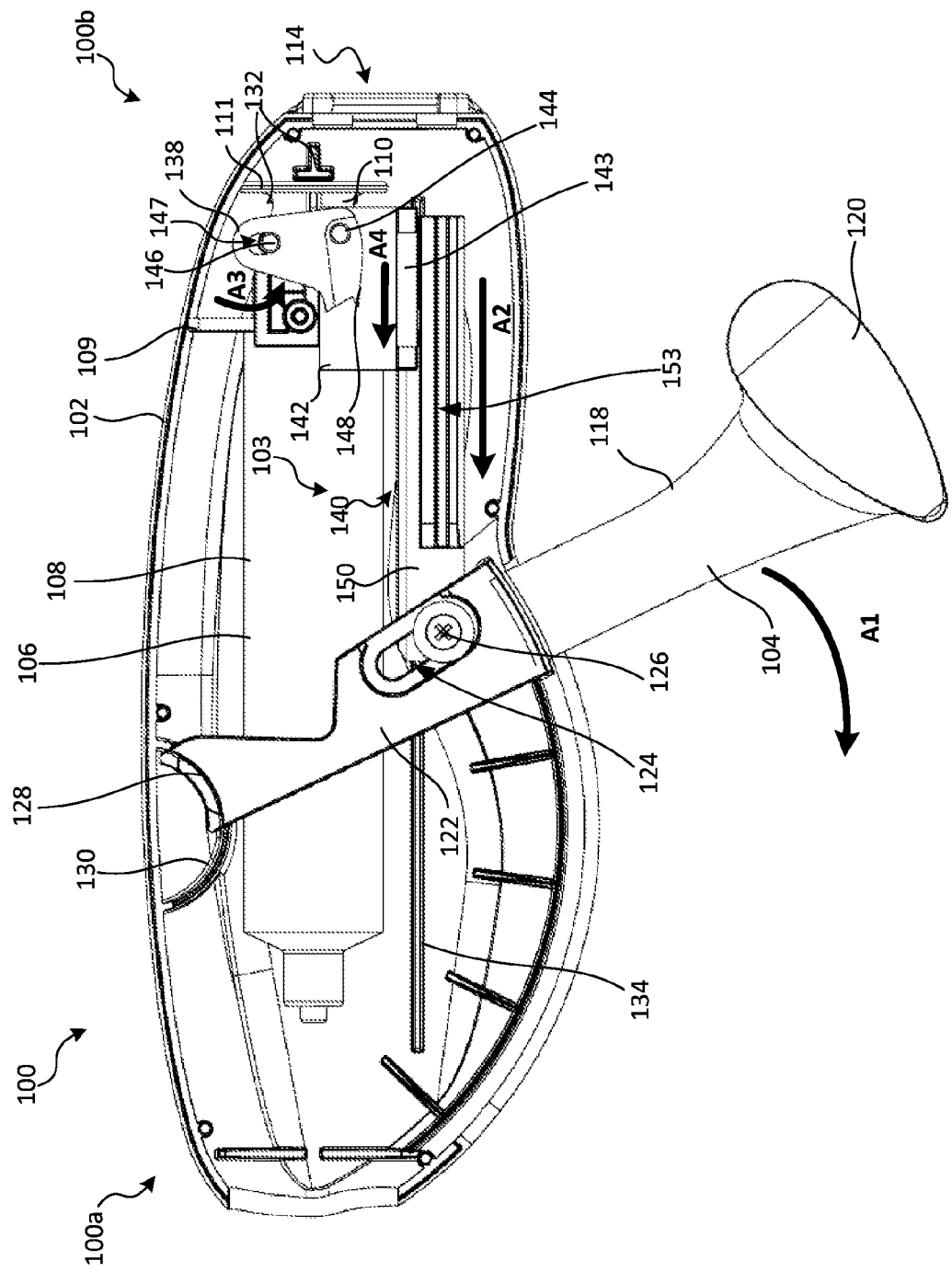
FIG. 3A is a side view of the retraction and aspiration device of FIGS. 1A-1B shown in a first state with a portion of the housing removed for purposes of illustration.
Figure 3B:
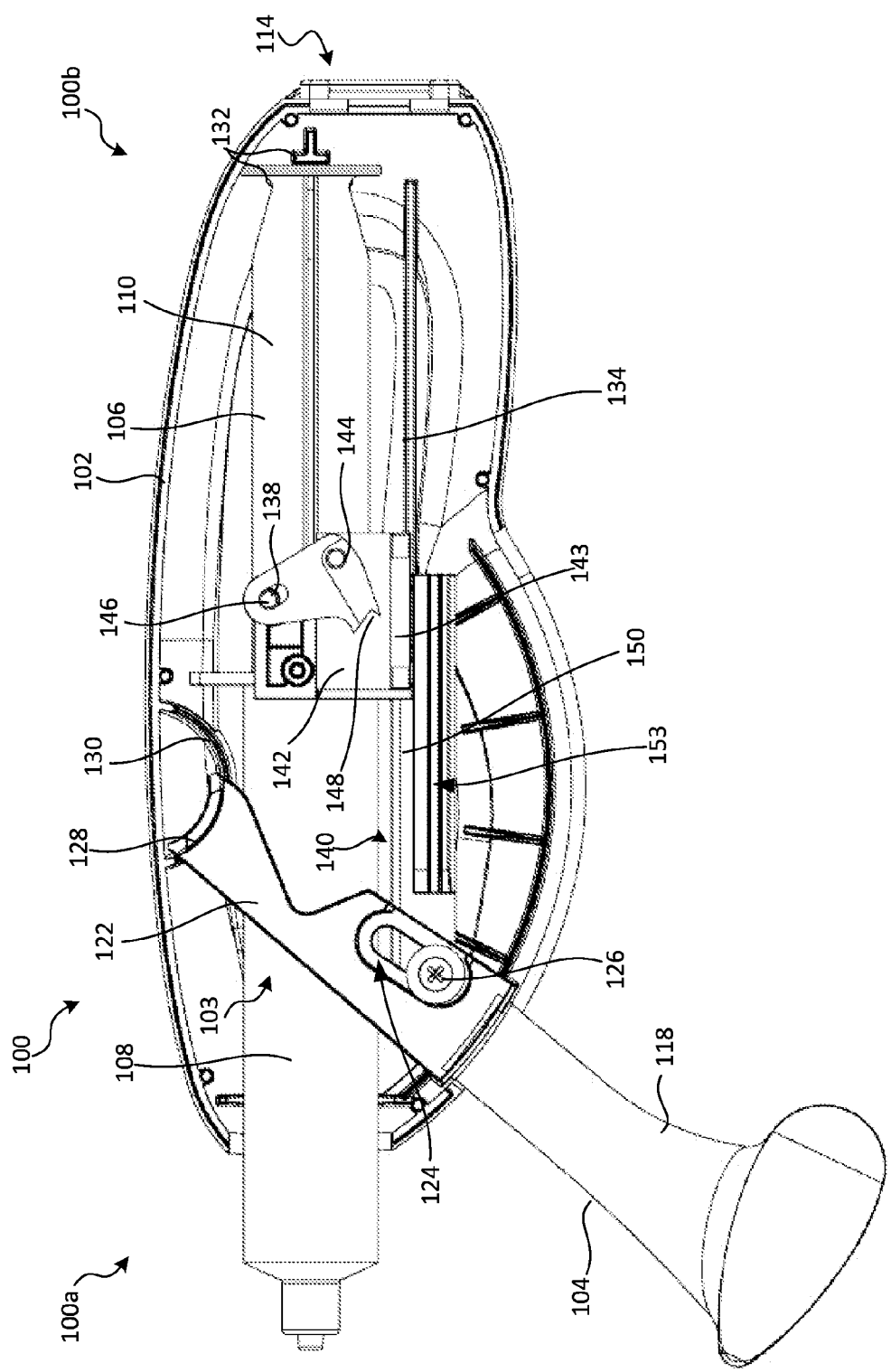
FIG. 3B is a side view of the retraction and aspiration device of FIGS. 1A-1B shown in an intermediate state with a portion of the housing removed for purposes of illustration.

Operation of the RA device 100 will now be described with reference to FIGS. 3A-3B. FIGS. 3A-3B are side views of the RA device 100 of FIGS. 1A-1B shown in a first and second state, respectively, with a portion of the housing 102 removed for purposes of illustration. As shown in FIG. 3A, when the lever 104 is in the first position, the pressure source 106 is not activated (e.g., generating pressure), and the cam 138 is disengaged from the catheter C to allow axial movement of the adjacent catheter component(s) relative to the second slider 142. When the lever 104 is rotated away from the housing 102 toward the second position (indicated by arrow A1), the first slider 140 moves axially (indicated by arrow A2) in a proximal direction, thereby pulling the pin 146 and the first slider 140 (FIGS. 2A-2B) proximally relative to the housing 102.

As the pin 146 slides proximally, the cam 138 slides along the pin 146 (via slot 147), thereby rotating the cam 138 counterclockwise around the pin 144 (indicated by arrow A3). As the cam 138 rotates, the locking portion 148 contacts a first portion of the catheter (not shown) and clamps the first portion of the catheter against a portion of the second slider 142. The cam 138 continues to rotate until the pin 146 reaches a top end of the slot 147. The length of the slot 147 and/or the distance between the locking portion 148 and an outer surface of the adjacent catheter limits the rotation of the cam 138, and separation of the first and second sliders 140, 142. The pin 136 exerts a proximal force on the cam 138, which moves the cam 138 and pulls the second slider 142 proximally via the pin 144 (indicated by arrow A4). Because the first portion of the catheter is trapped against the second slider 142 by the locking portion 148 of the cam 138, proximal movement of the second slider 142 retracts the catheter.

As the pin 146 is sliding proximally, the second portion 154 also slides proximally, thereby pulling the flange 109 of the barrel 108 proximally to separate the barrel 108 from the plunger 110. Proximal movement of the barrel 108 relative to the plunger 110 creates a negative pressure at an outlet portion of the barrel 108 which, as described below, can be used to aspirate a lumen of the catheter.

As shown in FIG. 3B, when the lever 104 is in the second position, the pressure source 106 is in the second position and not activated, and the locking portion 148 of the cam 138 prevents axial movement of the catheter relative to the second slider 142. When the lever 104 is rotated toward the housing 102 (toward the first position), the first slider 140 moves distally, thereby pushing the pin 146 distally and causing the cam 138 to slide along the pin 146 (via the slot 147), thereby rotating the cam 138 clockwise about pin 144. Rotation of the cam 138 clockwise causes the locking portion 148 to disengage the first portion of the catheter that was previously clamped between the locking portion 148 and the second slider 142. It will be appreciated that the present disclosure is not limited to the directional terms of "clockwise" and "counterclockwise". For example, in some embodiments, the cam 138 can rotate clockwise to engage the catheter and counterclockwise to disengage the catheter.

Because the locking portion 148 disengages the first portion of the catheter that was previously clamped between the locking portion 148 and the second slider 142, when the lever 104 is rotated from the second position to the first position the first slider 140 moves distally (towards its starting position) without moving the catheter. Thus, the next time the lever 104 is rotated away from the housing 102, the cam 138 will engage a new portion of the catheter such that the catheter is incrementally retracted proximally each time the lever 104 is moved towards the second position. Such non-continuous, synchronized aspiration and retraction can be advantageous because it reduces the amount of fluid withdrawn from the patient's body during treatment. In addition, it may be advantageous to consolidate the steps and motions required to both mechanically transport the thrombus into the aspiration lumen of the catheter system and remove fluid from the aspiration lumen into one motion by one person.

II. Selected Embodiments of Retraction/Aspiration Systems and Methods of Use

Figure 5A:
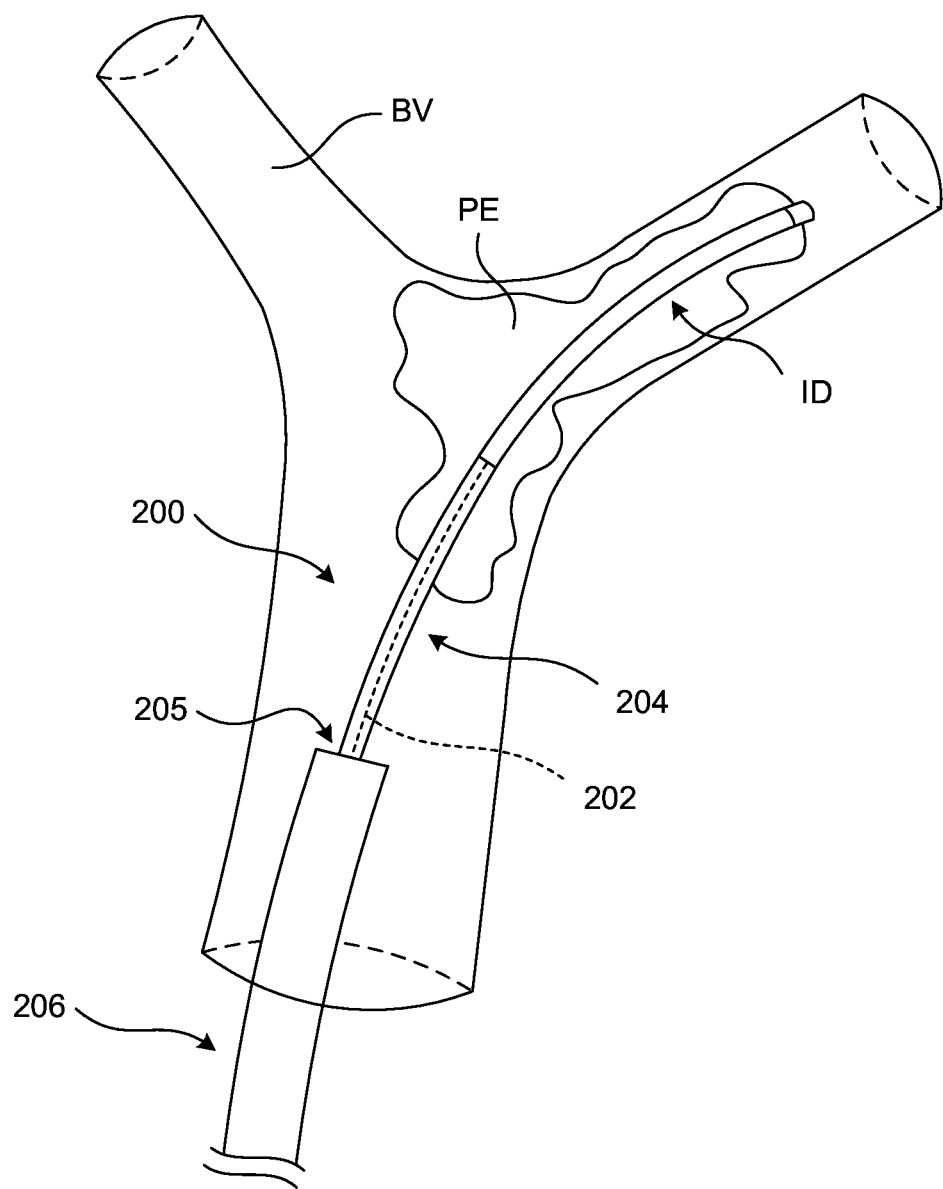
FIGS. 5A-5G are schematic illustrations of a distal portion of the retraction and aspiration system during a clot removal procedure in accordance with the present technology.

FIG. 5A is a side view of a distal portion of a catheter system 200 positioned adjacent an embolism or clot material PE within a pulmonary blood vessel BV. As shown in FIG. 5A, the catheter system 200 can include an outer guide catheter 206 defining a lumen 205, a delivery sheath 204 slidably received within the lumen of the guide catheter 206, and an elongated push (and/or pull) member 202 slidably received within a lumen of the delivery sheath 204. The guide catheter 206 and the delivery sheath 204 individually comprise an elongated shaft having a lumen and, in some embodiments, the push member 202 can also define a lumen (e.g., configured to receive a guidewire therethrough). In a particular embodiment, the catheter 200 does not include a guide catheter 206 and/or a delivery sheath 204. As shown in FIG. 5A, a distal portion of the push member 202 can be integral with or coupled to an interventional device ("ID"), such as a clot removal and/or clot treatment device, that is housed within the delivery sheath 204. Accordingly, axial movement of the push member 202 causes axial movement of the interventional device ID.

As shown in FIG. 5A, the delivery sheath 204 and interventional device ("ID") (such as, for example, a clot treatment device), can be positioned at least partially within the clot material PE. Access to the pulmonary vessels can be achieved through the patient's vasculature, for example, via the femoral vein. The catheter system 200 can include an introducer 210 (FIG. 4A) that can be partially inserted into the femoral vein. A guidewire (not shown) can be guided into the femoral vein through the introducer 210 and navigated through the right atrium, the tricuspid valve, the right ventricle, the pulmonary valve and into the main pulmonary artery. Depending on the location of the embolism, the guidewire can be guided to one or more of the branches of the right pulmonary artery and/or the left pulmonary artery. It will be understood, however, that other access locations into the venous circulatory system of a patient are possible and consistent with the present technology. For example, the user can gain access through the jugular vein, the subclavian vein, the brachial vein or any other vein that connects or eventually leads to the superior vena cava. Use of other vessels that are closer to the right atrium of the patient's heart can also be advantageous as it reduces the length of the instruments needed to reach the pulmonary embolism.

Figure 5B:
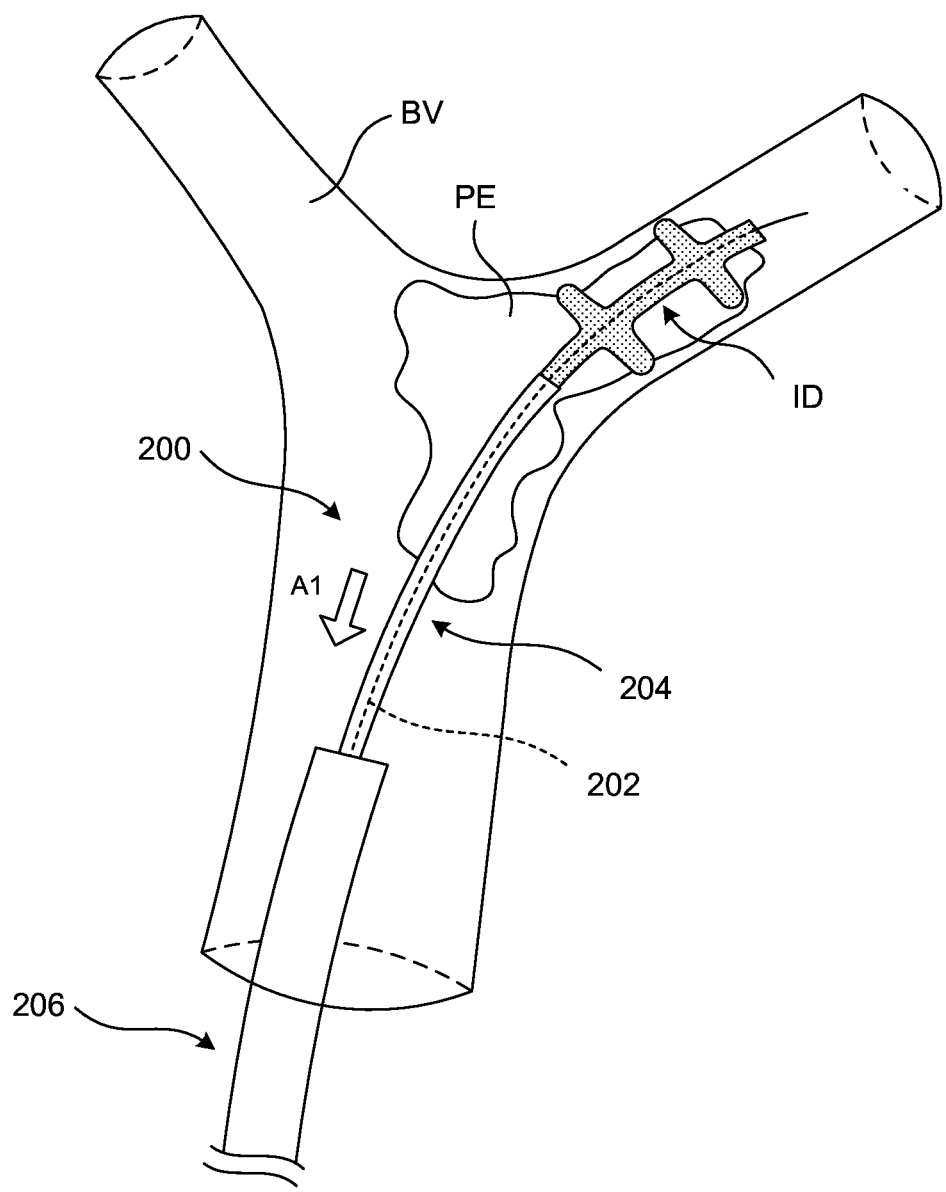
Figure 5C:
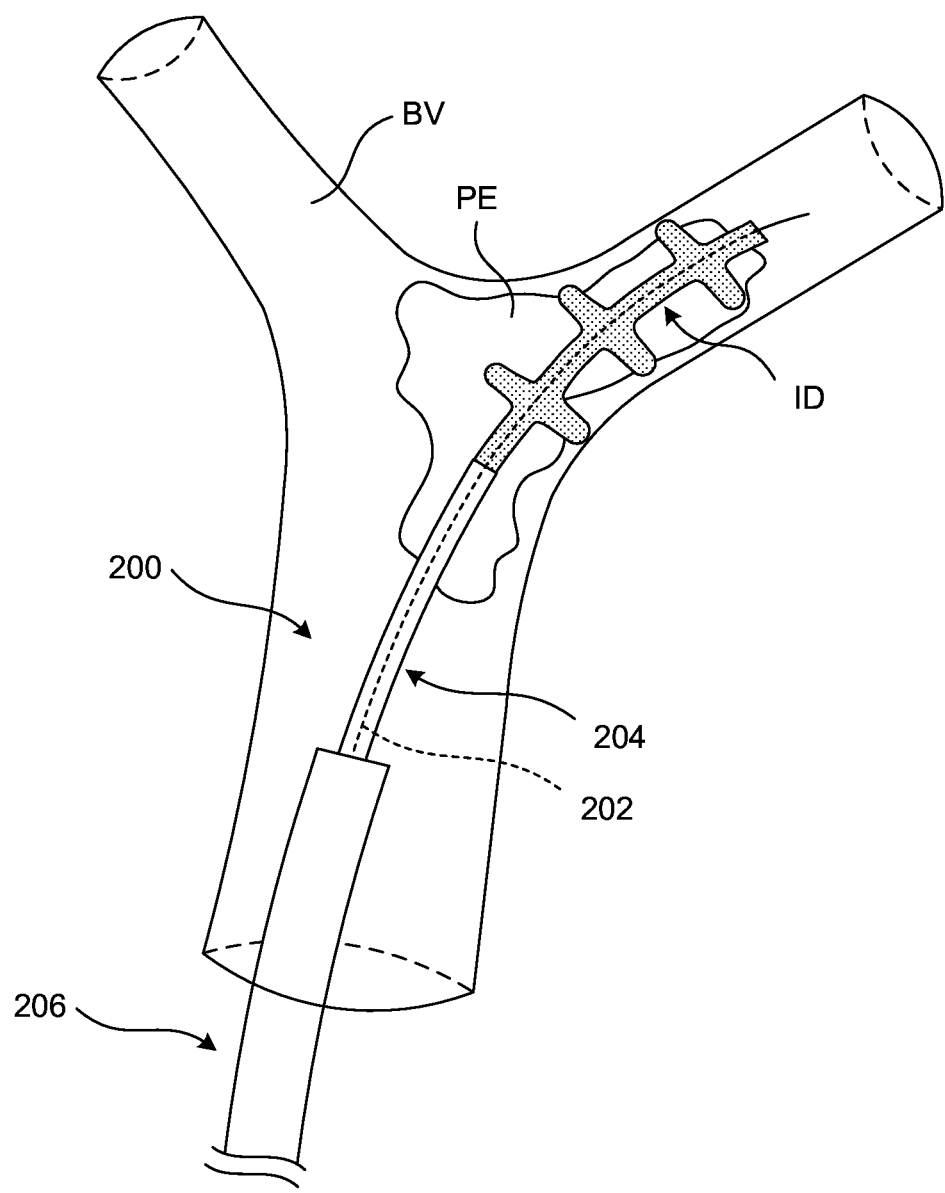
Figure 5D:
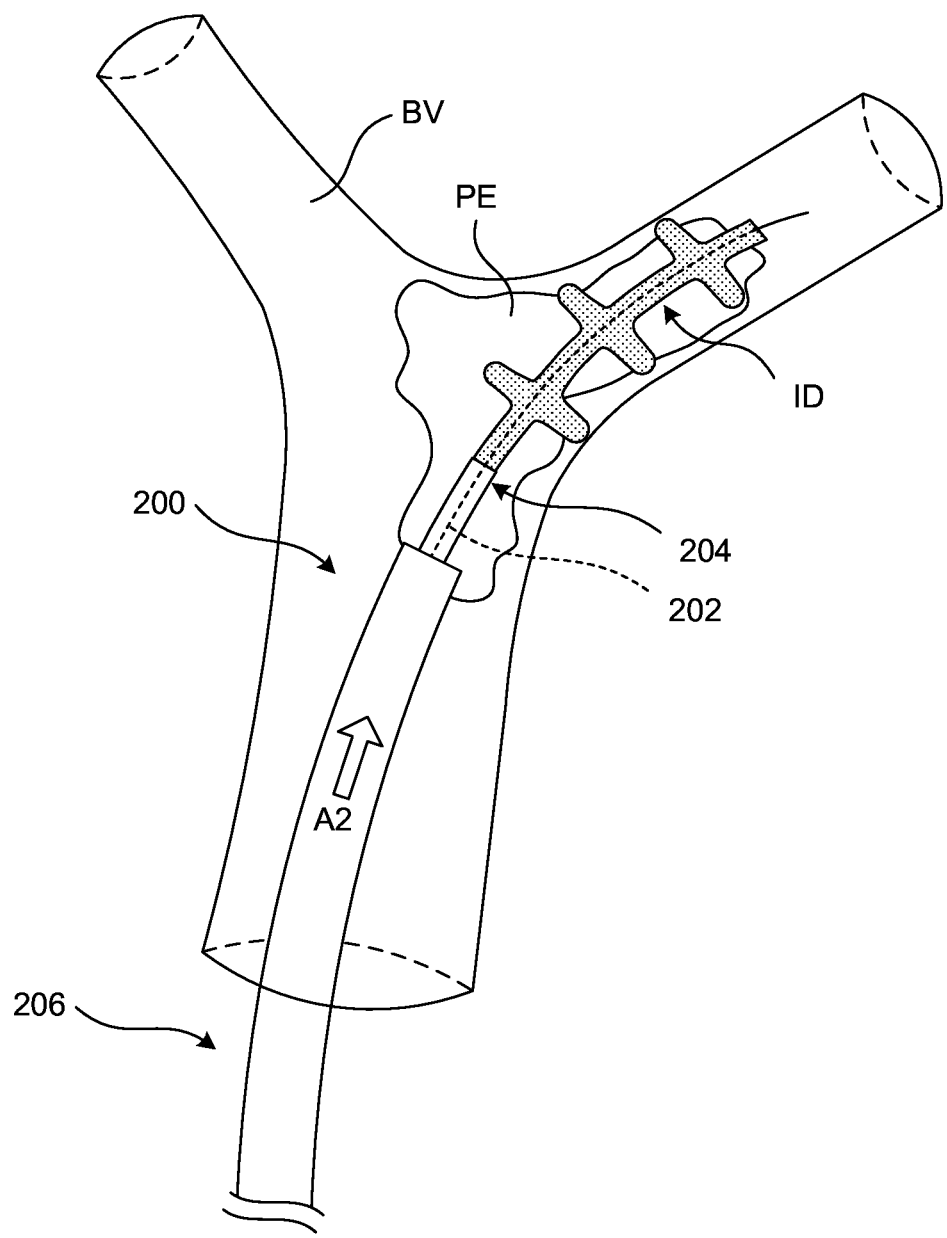

As shown in FIGS. 5B-5C, the delivery sheath 204 can be withdrawn proximally (indicated by arrow A1 in FIG. 5B) to allow the ID to expand within the clot material PE, thereby grabbing the nearby clot material PE. Although FIG. 5B shows the ID positioned at the treatment site such that a distal terminus of the ID is distal to a distal terminus of the clot material PE, in some procedures the ID may be positioned such that the distal terminus of the ID is proximal of the distal terminus of the clot material PE. As shown in FIG. 5D, in some embodiments the guide catheter 206 can optionally be advanced distally (indicated by arrow A2) to a proximal portion of the clot material PE.

Figure 4A:
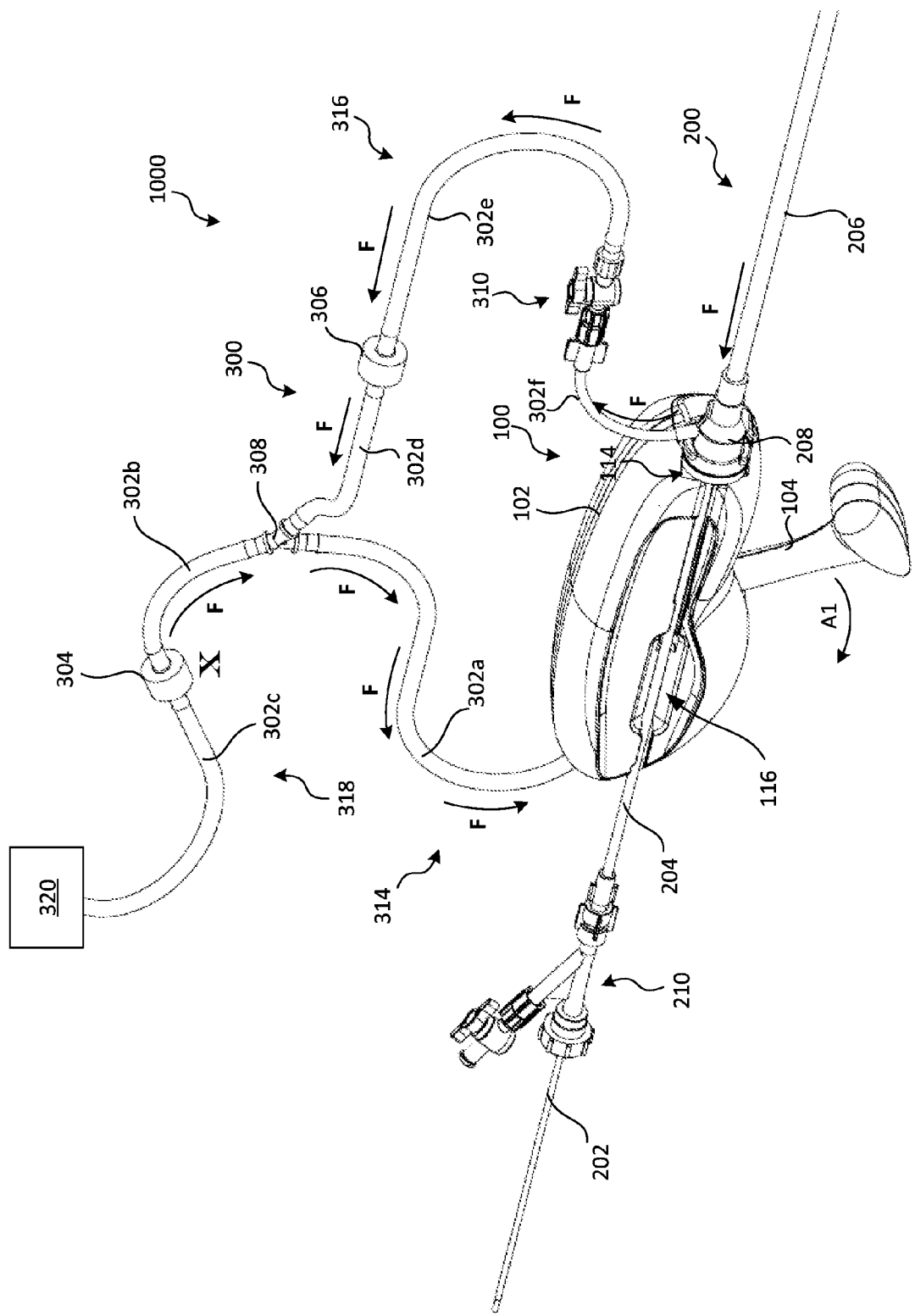
FIG. 4A is a perspective view of a retraction and aspiration system configured in accordance with the present technology shown in a first state.
Figure 4B:
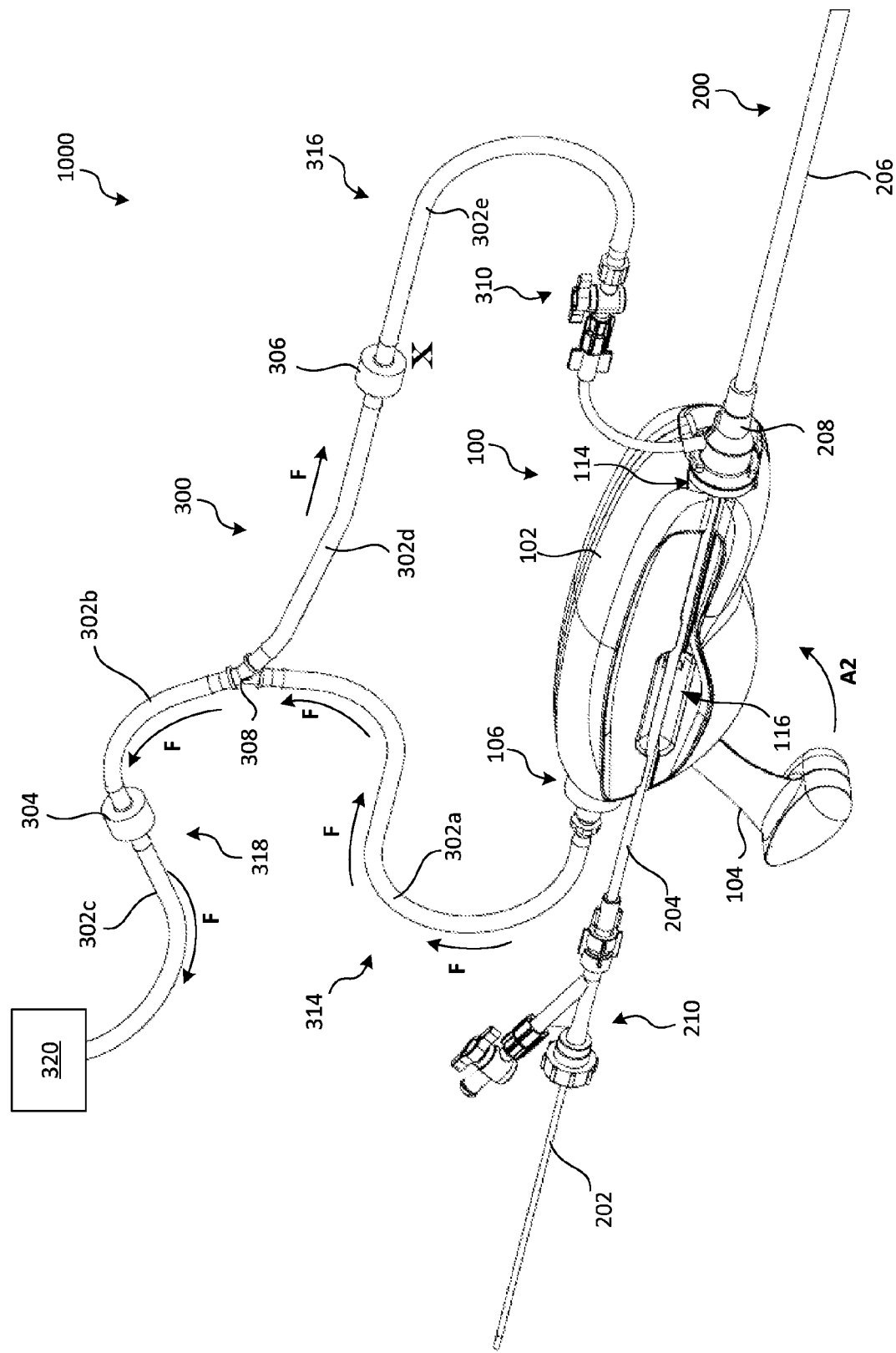
FIG. 4B is a perspective view of the retraction and aspiration system shown in FIG. 4A in a second state.

FIGS. 4A-4B are perspective views of a proximal portion of a retraction and aspiration system 1000 (also referred to herein as the "RA system 1000") configured in accordance with the present technology, shown with the RA device 100 in a first state and a second state, respectively. Referring to FIGS. 4A-4B, the RA system 1000 can include the RA device 100, the catheter system 200, and a tubing system 300. A proximal portion of the guide catheter 206 can be received by a distal portion 100b (FIG. 1B) of the RA device 100. For example, a proximal portion of the guide catheter 206 can include an attachment piece 208 that is configured to be detachably coupled to the RA device 100 (e.g., via a snap-fit arrangement) to secure the catheter 200 to the RA device 100. The attachment piece 208 can also fluidly connect the aspiration lumen to the tubing system 300 of the RA system 1000. The push member 202 and ID can be pre-loaded into the delivery sheath 204, and the delivery sheath 204 can be fed distally through the channel 116 (either via the proximal end of the channel 116 or first pushed sideways through a portion of the channel 116) and into the guide catheter 206.

The tubing system 300 fluidly couples the pressure source 106 to an aspiration lumen of the catheter 200 (e.g., the lumen of the guide catheter 206). The tubing system 300 has a first portion 314 coupled to the pressure source 106, a second portion 316 coupled to the catheter 200, and a drainage portion 318 coupled to a reservoir 320 (e.g., a vinyl bag). The first portion 314, second portion 316, and/or drainage portion 318 can include one or more tubing sections (labeled individually as tubing sections 302a-302f) and/or fluid control means, such as one or more control valves. For example, the first portion 314 can include tubing section 302a, the drainage portion 318 can include tubing section 302b, first valve 304, and tubing section 302c, and the second portion 316 can include tubing section 302d, second valve 306, tubing section 302e, stop-cock 310, and tubing section 302f. The first valve 304 can be a one-way valve (e.g., a check valve) that only allows fluid flow from the first portion 314 to the drainage portion 318 (and not vice-versa). The second valve 306 can also be a one-way valve (e.g., a check valve) that only allows flow from the second portion 316 to the drainage portion 318 (and not vice-versa). A Y-connector 308 can fluidly couple the first, second and drainage portions 314, 316, 318. In other embodiments, the first, second and/or drainage portions 314, 316, 318 can have more or fewer tubing sections, connectors and/or fluid control means and/or other suitable configurations.

Figure 5E:
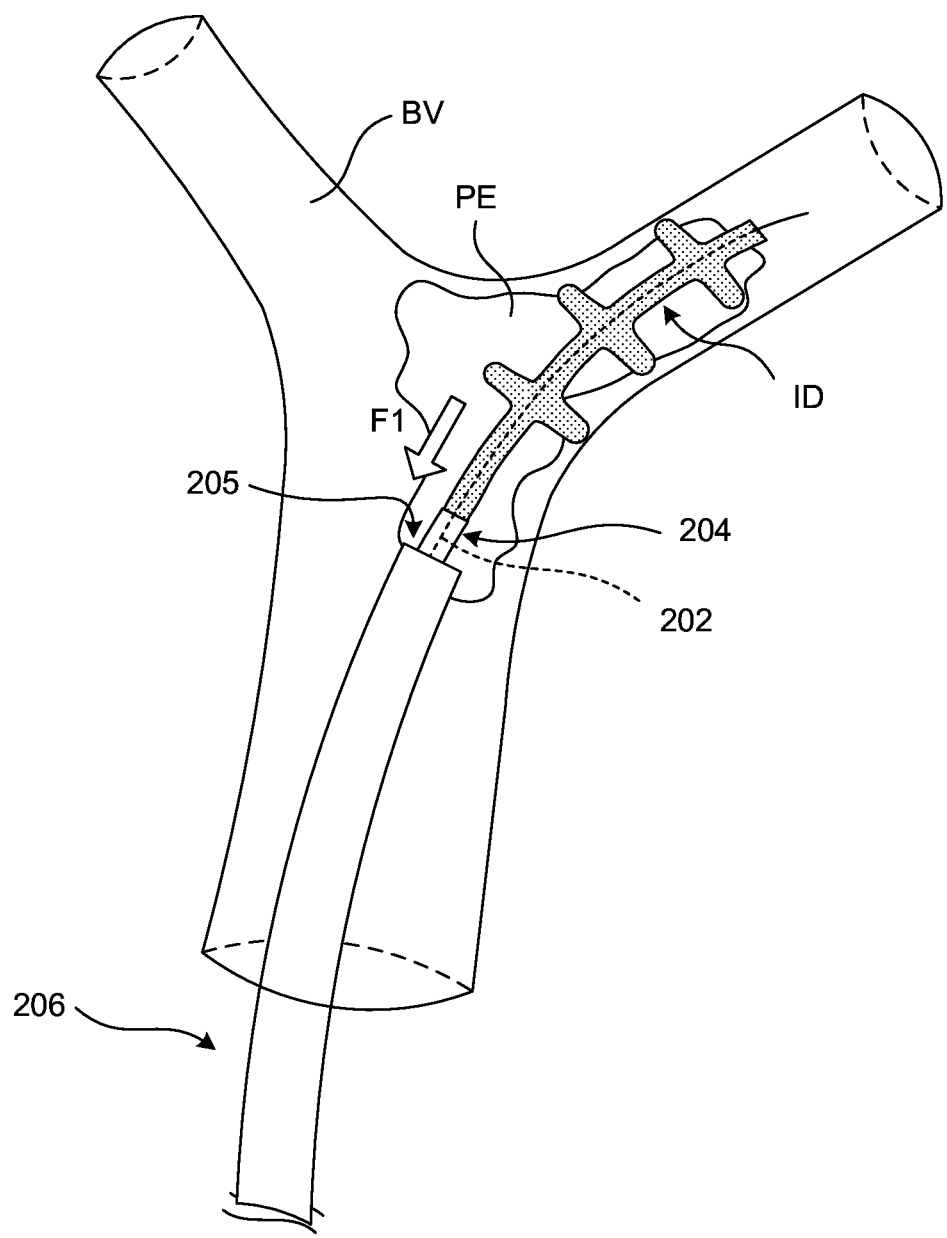

As shown in FIGS. 4A and 5E, moving the lever 104 from the first position to the second position (indicated by arrow A1) simultaneously (1) generates a negative pressure in the aspiration lumen 205 of the guide catheter 206 (indicated by arrows F in FIG. 4A and F1 in FIG. 5E), and (2) retracts the delivery sheath 204 and/or push member 202, thereby retracting the ID from the treatment site. Specifically, when the lever 104 is rotated away from the housing 102 toward the second position, the first slider 140 moves axially in a proximal direction, thereby rotating the cam 138 (FIGS. 2A-2B) and causing the locking portion 148 to engage the delivery sheath 204 and/or the push member 202 such that the delivery sheath 204 and/or push member 202 is trapped against the second slider 142 (FIGS. 2A-2B) by the locking portion 148 of the cam 138. Depending on the embodiment of the catheter 200, the locking portion 148 can engage and secure the push member 202 directly or indirectly. For example, in those embodiments not including a delivery sheath 204, the locking portion 148 can directly contact the push member 202 (and thus the push member 202 directly contacts the second slider 142). In the embodiment shown in FIGS. 4A-4B, the locking portion 148 directly contacts the delivery sheath 204 and exerts a compressive force on the delivery sheath 204 that affects the push member 202, thereby also preventing axial movement of the push member 202. In yet other embodiments, the actuation mechanism 103 and/or cam 138 can be configured such that the locking portion 148 exerts only enough force to trap the delivery sheath 204 and not the push member 202.

Accordingly, as the lever 204 moves to the second position, the lever 204 pulls the delivery sheath 204 and/or push member 202 proximally while simultaneously generating a negative pressure (arrows F) in the aspiration lumen 205. During this time, the guide catheter 206 remains fixed (by the housing 102) relative to the delivery sheath 204 and push member 202. As such, as the lever 204 moves from the first position to the second position, the ID, delivery sheath 204, push member 202, and clot material PE are drawn proximally into the guide catheter 206.

Figure 5F:
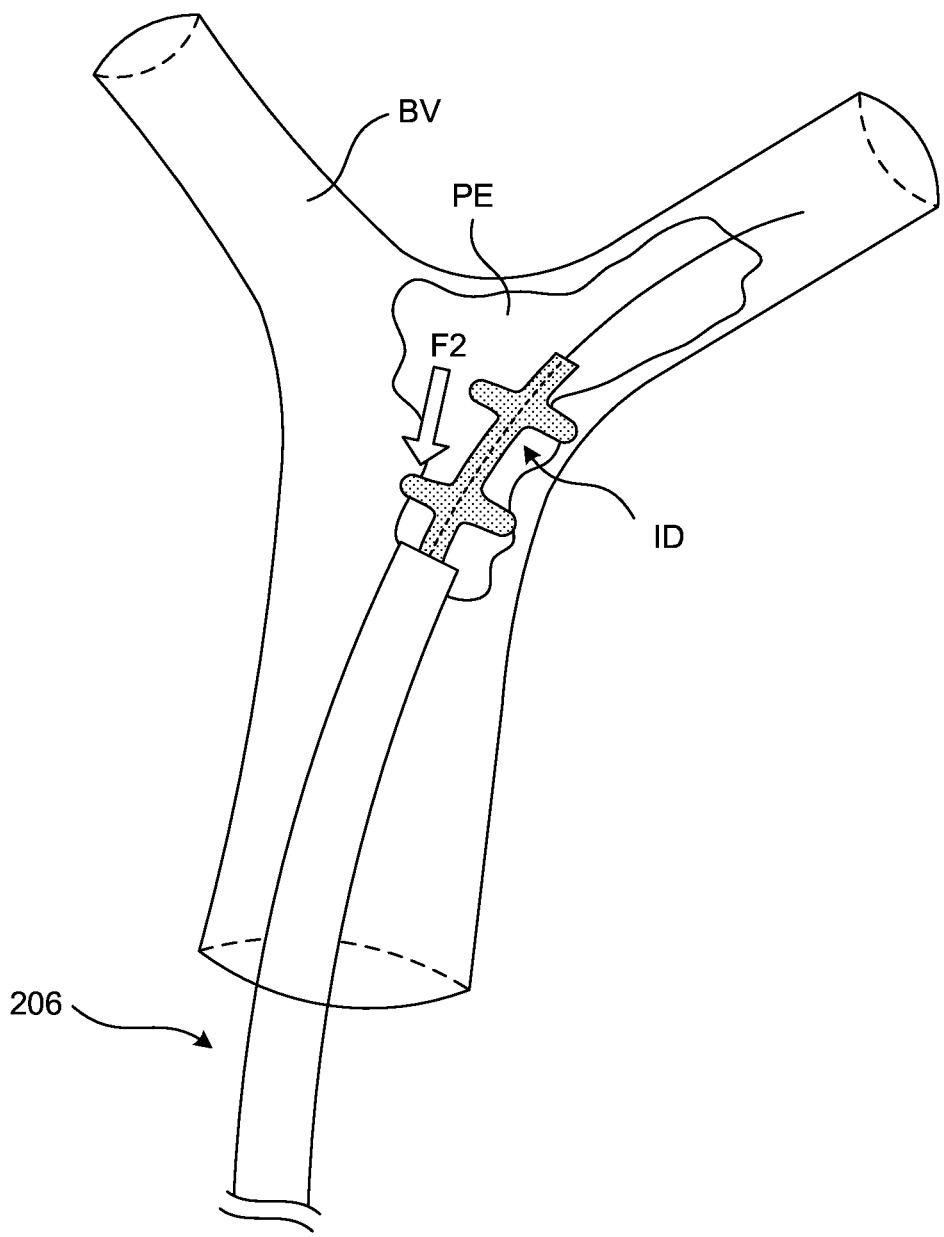
Figure 5G:
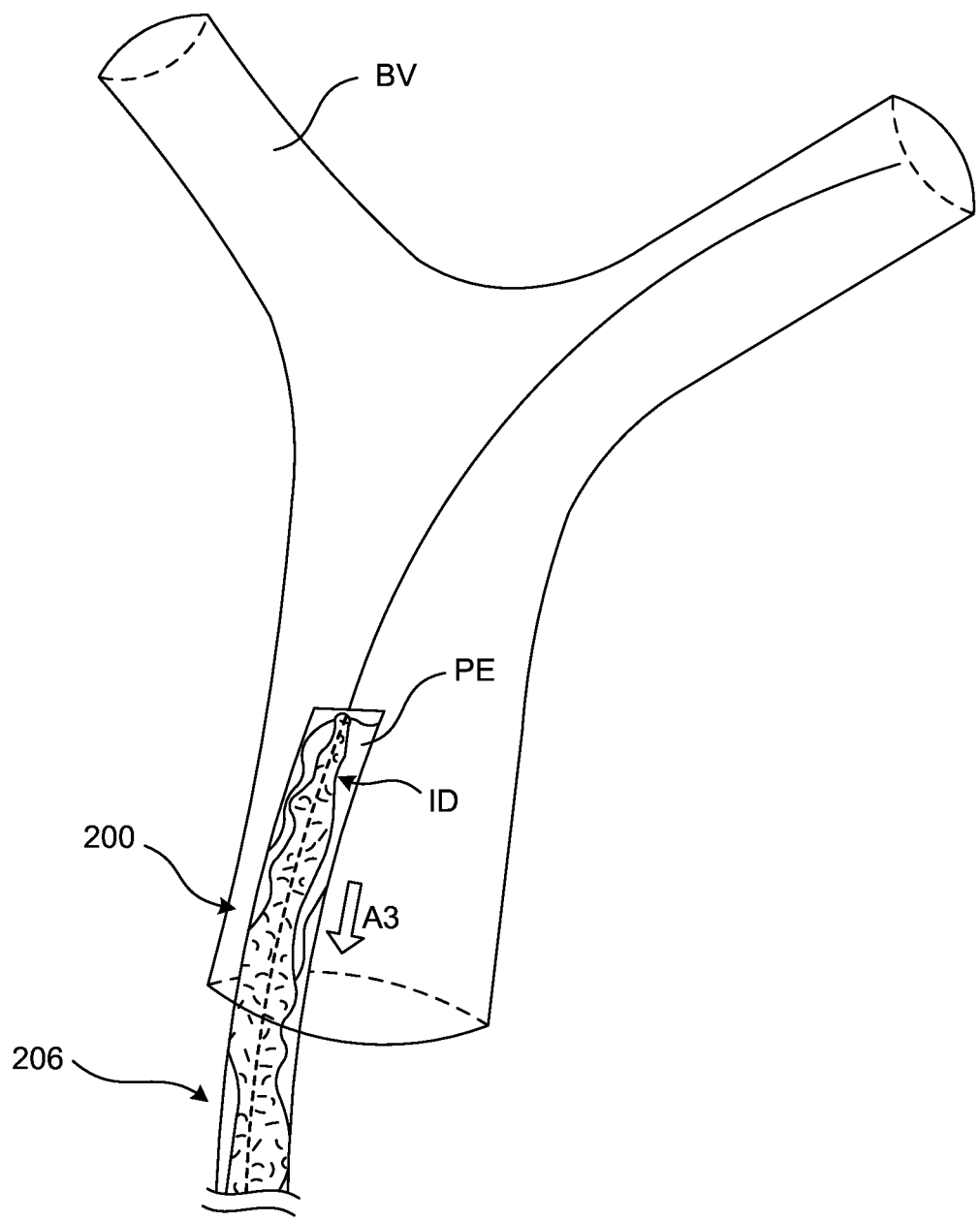

As shown in FIG. 4B, moving the lever 104 from the second position to the first position (indicated by arrow A2) creates a positive pressure (indicated by arrows F in FIG. 4B) in the first portion 314 and drainage portion 318 of the tubing system 300. The second valve 306 prevents the positive pressure from affecting the aspiration lumen, thereby preventing the backflow of fluid into the blood vessel BV at the treatment site. With respect to the catheter system 200, when the lever 104 is rotated from the second position to the first position, the first slider 140 moves distally (towards its starting position) without moving the delivery sheath 204 and push member 202. Thus, the next time the lever 104 is rotated away from the housing 102, the cam 138 (FIGS. 2A-2B) will engage a new portion of the delivery sheath 204 and push member 202 such that the delivery sheath 204 and push member 202 are incrementally retracted proximally each time the lever 104 is "pumped" (e.g., moved from the first position to the second position and then back to the first position). Once the clot material PE is positioned within the guide catheter 206 such that a distal terminus of the clot material PE is proximal from a distal terminus of the guide catheter 206, the catheter system 200 can be withdrawn proximally (indicated by arrow from the treatment site, as shown in FIG. 5G) and removed from the patient.

Depending on the size of the thrombus, local anatomical and/or physiological conditions, and position of the ID relative to the clot material, the lever 104 can be pumped several times to fully extract the thrombus and/or ID from the treatment site. For example, FIGS. 5D-5E show the proximal movement of the delivery sheath 204, push member 202, and ID after a first pump of the lever 104. FIGS. 5E-5F show the proximal movement of the delivery sheath 204, push member 202, and ID after a second pump of the lever 104 (second instance of pressure generation indicated by arrows F1 and F2 in FIGS. 5E and 5F, respectively). In some embodiments, the ID and clot material PE can be fully withdrawn into the guide catheter 206 after a single pump of the lever 104. In other embodiments, such as those procedures where the ID is initially positioned such that a distal terminus of the ID is proximal of a distal terminus of the clot material PE (the clot material PE often originates in a vein of the patient's leg, and thus is cast into an elongated, worm-like shape), it can take several pumps of the lever 104 to fully withdraw the clot material PE into the guide catheter. Thus, in some embodiments, even when the ID is positioned within the guide catheter 206 such that a distal terminus of the ID is proximal of the distal terminus of the guide catheter 206, the lever 104 can be pumped several more times to continue to withdraw the clot material PE into the guide catheter 206.

It will be appreciated that the lever 104 need not move the entire distance from the first position to the second to generate pressure and retract the device. In some procedures, it may be beneficial for the clinician to move the lever 104 a portion of the distance between the first and second positions to effect a reduced retraction distance and/or reduced aspiration volume (as compared to a full movement from the first position to the second position). Likewise, the clinician can begin movement of the lever 104 towards the first position when the lever 104 is in any position (and not just from the second position). For example, a clinician can rotate the lever 104 from the first position to a position halfway between the first and second position, then move the lever 104 back to the first position.

The RA device 100 and associated methods and systems of the present technology provide several advantages over conventional systems. First, the RA device 100 of the present technology is configured to apply negative pressure only while the catheter system (or a component thereof) is being retracted. Therefore, when retraction pauses or stops altogether, aspiration also pauses or stops altogether. As such, aspiration is intermittent and discrete (e.g., non-continuous) and dependent upon retraction of a delivery sheath and/or interventional device. Such non-continuous, synchronized aspiration and retraction can be advantageous because it reduces the amount of fluid (e.g., blood and other fluids present in the blood vessel at the treatment site) withdrawn from the patient's body during treatment. Conventional automatic and/or continuous aspiration devices aspirate large volumes of blood that may then require the blood to be filtered and re-infused or otherwise replaced. Infusion of new or filtered blood complicates the procedure and may increase cost due to the need for a perfusionist.

The RA device 100 can complete a pass (e.g., from the first movement of the lever 104 toward the second position to the point where the ID and the clot have been withdrawn into the guide catheter 206 such that the distal termini of the ID and the clot are proximal of the distal terminus of the guide catheter) within 1 to 8 pumps or activations of the lever 104 (i.e., moving the lever 104 from the first position to the second position). In some embodiments, the RA device 100 can complete a pass within 3-6 activations of the lever 104. Thus, in those embodiments where the pressure source 106 is a syringe having a 20 cc barrel, each pump of the lever 104 results in about 10 cc to about 20 cc of fluid removal (the actual usable volume of a 20 cc barrel can be closer to 15 cc to 18 cc). Accordingly, depending on the number of pumps of the lever 104 required in a pass (which depends on the size and density of the clot and the local anatomy and/or physiology), and again assuming a 20 cc barrel (although other volumes are within the scope of the present technology), the RA system 1000 and/or RA device 100 can aspirate between about 10 cc and about 300 cc of fluid per pass using a 20 cc syringe, and in some embodiments between about 20 cc and about 120 cc of fluid per pass. Moreover, the RA device 100 and/or the RA system 1000 provides an aspiration flow rate of between about 300 cc/min and 1500 cc/min, and in some embodiments between about 500 cc/min and about 1000 cc/min.

Another advantage is that the RA device 100 and/or RA system 1000 allows for simultaneous aspiration (through the catheter) and retraction of at least a portion of the catheter (e.g., an interventional device coupled to an elongated shaft of the catheter). The RA device 100 combines these functions in one, hand-held apparatus that makes it easier to use and more efficient than doing separate mechanical operations such as manual retraction and syringe aspiration. Doing manual retraction and syringe aspiration as has been known in the art is cumbersome and generally requires two people.

Additionally, the RA device 100 and associated systems and methods can rapidly reduce the Mean Resting Pulmonary Artery Pressure (MRPAP). In some embodiments, the RA device 100 and associated systems and methods may provide a greater reduction of MRPAP than existing treatments due to the rapid restoration of at least some blood flow, disruption or breakup of thrombus, increased thrombus surface area and removal of thrombus by aspiration and/or capture and retraction. It will be appreciated that the disruption and breakup of thrombus is a natural result of the engagement, retraction and aspiration with the RA system 100 and should be distinguished from conventional devices that actively cut small fragments from the thrombus when the device expands and capture these fragments inside the device. In some embodiments, MRPAP may be reduced shortly after deployment or within about 1 hour after deployment, herein referred to as "acute MRPAP reduction". In some embodiments, this acute MRPAP reduction may be between about 10% and about 30%. In some embodiments, MRPAP reduction may be between about 20% to about 50% after about 8 hours post procedure. This may be a substantially faster reduction of MRPAP than thrombolytic drug therapy or thrombolysis systems can provide. In the European Heart Journal, Engelberger et al. reported MRPAP reduction in pulmonary embolism patients of about 32% at 24 hours post-procedure with an EkoSonic MACH4 Endovascular Systems (EKOS Corporation; Bothell, Wash.) and thrombolytic drug rtPA. After 24 hours, the method and device in accordance with the present invention may, in some embodiments reduce MRPAP by about 35% to about 50% and in other embodiments by about 40% to about 60%.

Yet another advantage of the RA device 100 of the present technology is its ability to provide tactile feedback to the clinician so that the clinician can gauge tension on the push member 202. For example, if the clot PE is stuck (for any reason), the clinician can feel resistance in the lever 104 as the clinician attempts to move the lever 104 to the second position. Based on this feedback, the clinician may decide to stop the procedure and/or readjust a portion of the catheter system 200. Additionally or alternatively, one or more embodiments of the RA device 100 and/or RA system 1000 can include an automatic force feedback system that monitors the retraction force and automatically limits tension on the push member 202 and/or electromechanically releases the secured catheter component from the locking portion 148.

III. Selected Embodiments of Clot Treatment Devices

Although the RA system 1000 is described herein with reference to the catheter 200 coupled to the ID, the RA system 1000 and/or RA device 100 is configured for use with any catheter configured to support any ID. Examples of additional interventional devices, such as clot treatment devices, for use with the RA device 100 and/or RA system 1000 are detailed below.

Figure 6:
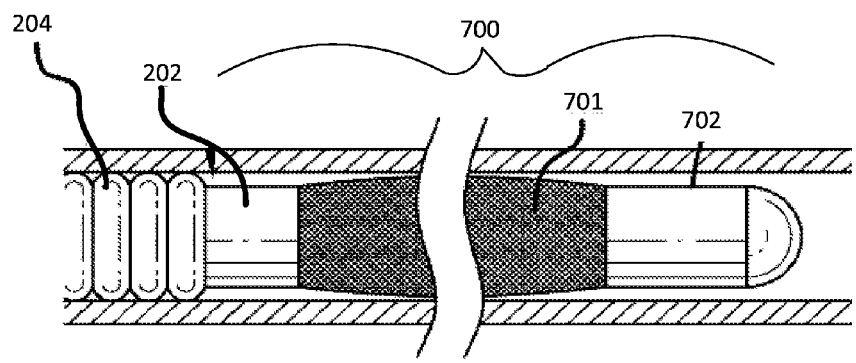
FIG. 6 is a side view of a clot treatment device configured in accordance with the present technology shown in a delivery state constrained within a delivery sheath.
Figure 7:
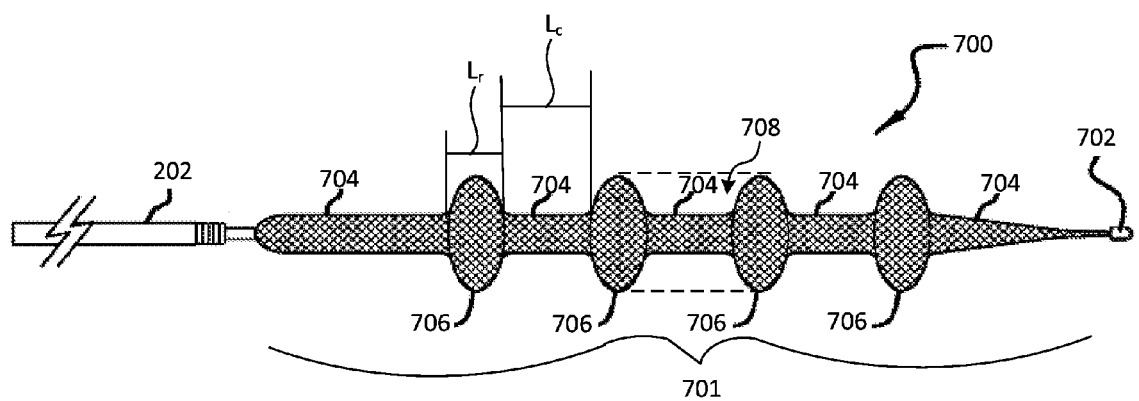
FIG. 7 is a side view of the clot treatment device shown in FIG. 6 in a deployed state.

FIGS. 6-7 show one embodiment of a clot treatment device 700 (also referred to herein as the "device 700") configured in accordance with the present technology, shown in a delivery state (constrained by the delivery sheath 204) and deployed state, respectively. As shown in FIGS. 6-7, the device 700 can include a self-expanding mesh 701 having a blunt distal tip 702. In some embodiments, the mesh 701 can be a braid of wires that are superelastic and/or made of shape memory material (e.g., nitinol, a cobalt chrome alloy, etc.). The distal termini of wires of the mesh 701 are secured by the distal tip 702, and the proximal termini of the wires of the mesh 701 can be fixed (directly or indirectly via an attachment member) to the push member 202 (FIGS. 4A-4B). In the illustrated embodiment, each of the push member 202 and the distal tip 702 define a central lumen for receiving a guidewire. In some embodiments, the device 700 can include a flexible sleeve (not shown) extending between the push member 202 and the distal tip 702. A proximal portion of the sleeve can be slidably positioned within the lumen of the push member 202, and a distal portion of the sleeve can be fixed to the distal tip 702. The sleeve and the elongated member 202 can have a telescoping arrangement such that, when the device 700 is deployed, the mesh 701 can elongate, compress, and flex along its longitudinal axis while still having the additional column support provided by the flexible sleeve.

Referring to FIG. 7, the mesh 701 can be generally cylindrical with a series of radially extending portions 706 situated along the axis of the device 700 and separated by a corresponding series of cylindrical portions 704. The mesh 701 can include a series of capture portions 708 between successive radially extending portions 706. Each capture portion 708 can be bound by the outer surface of the corresponding cylindrical portion 704 between the successive radially extending portions 706 and an imaginary outer periphery (shown as a dashed line) extending linearly between the radially-furthest portions of the successive radially extending portions 706.

The individual lengths $L_r$ of the radially extending portions can be less than the individual lengths $L_c$ of the cylindrical portions 704 that separate the radially extending portions 706. The portions of the mesh 701 proximal and distal to the proximal-most and distal-most radially extending portions 706, respectively, can have the same or different lengths, and can individually have lengths that are greater than, less than, or the same as the lengths of the cylindrical portions 704. The radially extending portions 706 provide a greater surface area along the device 700 than would a device without such portions (e.g., a device that is uniformly cylindrical with the same outside diameter as the cylindrical portions 704). As made clear by FIG. 7, the surface area to length ratio of each of the radially extending portions 706 is greater than the surface area to length ratio of each of the cylindrical portions 704. Accordingly, the radially extending portions 706 provide the mesh 701 with an increased surface area for engaging and/or gripping adjacent clot material, while the greater surface area to length ratio of the radially extending portions 706 versus the cylindrical portions 704 increases the volume of the capture portions 708, thus increasing the volume of clot material that can be trapped within the capture portions 708.

In the deployed state, the radially extending portions 706 can be sized to generally match the diameter of the target blood vessel (e.g., a pulmonary blood vessel, a cerebral blood vessel, etc.). In some embodiments, the radially extending portions 706 can individually have diameters slightly greater than the diameter of the target vessel so as to apply greater radial force against the blood vessel (without causing trauma). Similarly, in those circumstances involving smaller and/or delicate blood vessels, the radially extending portions 706 can have a diameter that is less than the diameter of the vessel at the target treatment site. It is contemplated that different sizes of the device 700 will be available for selection by the clinician for a particular presentation of the patient. Individual radially extending portions can have the same or different diameters.

Although four radially extending portions 706 and three cylindrical portions 204 are shown in FIG. 7, in other embodiments the mesh 701 can have more or fewer radially extending portions 706 and/or cylindrical portions 704. For example, in some embodiments the device 700 can have three radially extending portions 704 and two cylindrical portions 704. Moreover, although each of the radially extending portions 706 is generally disc-shaped in FIG. 7, in other embodiments the radially extending portions 706 can have other shapes and/or sizes so long as the surface area to length ratio of at least two successive radially-extending portions 706 remains greater than the surface area to length ratio of the corresponding cylindrical portion 704.

The generally cylindrical shape of the mesh 701 provides a flow lumen for blood across a clot during a clot treatment procedure. However, the clot treatment device 700 and/or mesh 701 can have other shapes, sizes, and/or configurations. For example, the mesh 701 and/or one or more portions of the mesh 701 (such as the cylindrical portions 704) can have a shape that is generally conical, generally concave or generally convex along its axis, so long as the shape provides the aforesaid lumen for blood flow.

Figure 8A:
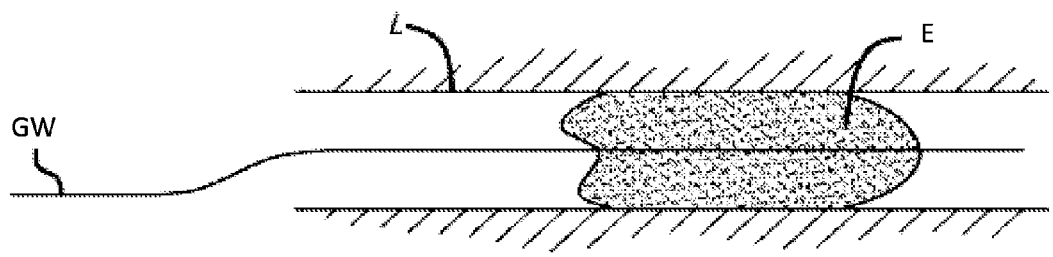
FIGS. 8A-8F illustrate a method for using the clot treatment device shown in FIGS. 6-7 and configured in accordance with the present technology to remove clot material from a vessel.
Figure 8B:
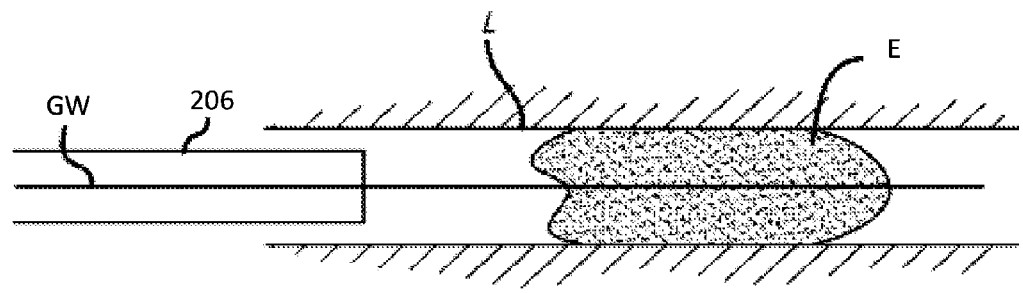
Figure 8C:
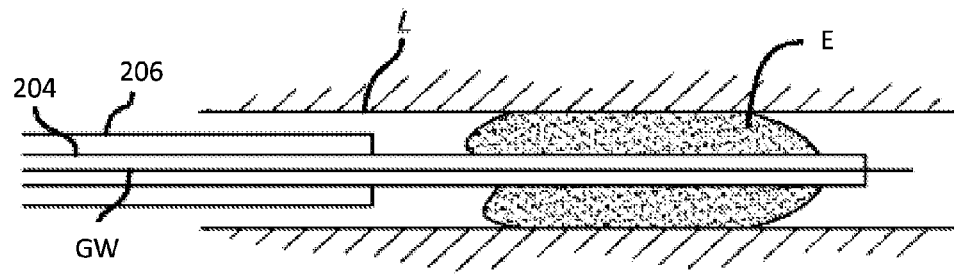

FIGS. 8A-8F show a method of using the clot treatment device 700 to treat a thromboembolism. As shown in FIG. 8A, a guidewire GW is extended through the clot in the blood vessel L. As shown in FIG. 8B, the guide catheter 206 can then be fed distally over the guidewire GW and moved to a location such that a distal terminus of the guide catheter 206 is positioned proximal to a distal terminus of the clot E.

At this point, the guidewire GW can optionally be withdrawn. However, in a particular embodiment shown in FIG. 8C, the guidewire GW remains and the delivery catheter 204 is then moved through the guide catheter 206 over the guidewire GW and pushed through the clot E.

Figure 8D:
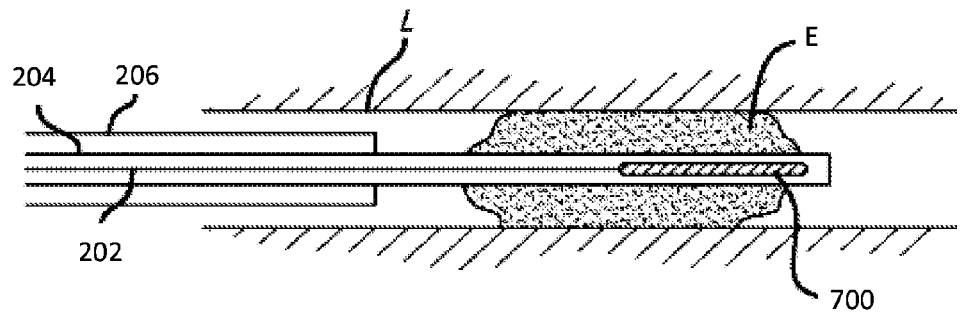
Figure 8E:
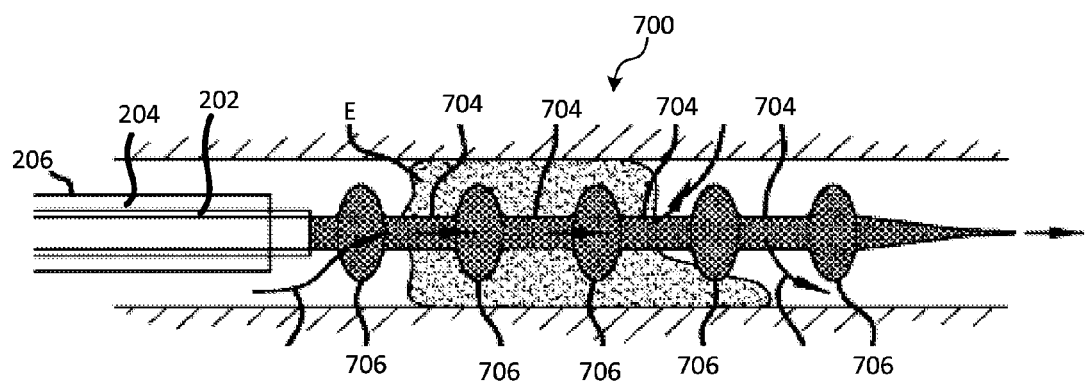

Referring to FIG. 8D, the guidewire GW is then withdrawn and the clot treatment device 700 is then moved through the delivery sheath 204 until the clot treatment device 700 is disposed proximate the distal terminus of the delivery sheath 204. The delivery sheath 204 is then retracted in a proximal direction while maintaining forward pressure on the clot treatment device 700 via the pusher member 202 so that the clot treatment device 700 becomes exposed and released from the delivery sheath 204. The clot treatment device 700 radially expands into the clot E and, in one embodiment, at least a portion of the clot treatment device 700 expands distally of the clot E. As shown in FIG. 8E, in some embodiments at least one of the radially extending portions 706 of the clot treatment device 700 are located distal to the clot E upon expansion of the clot treatment device 700.

It will be appreciated that upon expansion of the clot treatment device 700 as just described, fluid flow (e.g., blood flow) through the clot E is restored. This is depicted with arrows in FIG. 8E. More specifically, blood is now free to move through the mesh 701 of the clot treatment device 700 and exit the clot treatment device 700 distal to the clot E. As a result, the acute condition of blockage is corrected thus immediately improving the circulation of oxygenated blood in the patient.

The restoration of blood flow is anticipated to equate with restoration of a substantial portion of the normal blood flow rate for the patient. In less severe. i.e., "sub massive," pulmonary embolism patients, the clot treatment device 700 may increase blood flow rate by at least about 50 ml/min, at least about 150 ml/min or between about 100 to 250 ml/min. In severe, i.e., "massive," pulmonary embolism patients, a larger amount of the pulmonary artery flow is compromised. Hence, in some embodiments, at least about 500 ml/min of blood flow rate may be restored. Moreover, at least a portion of the flow restoration is expected to occur prior to the removal of the clot E, or any portion thereof.

Figure 8F:
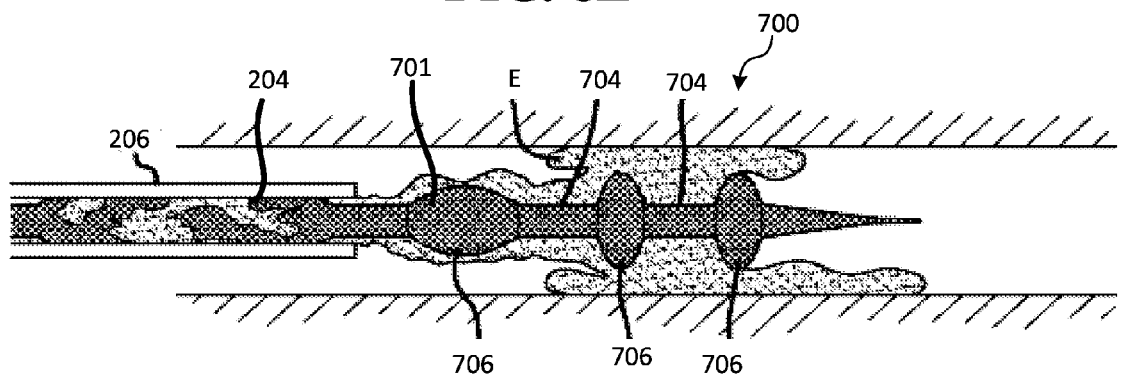

After the clot treatment device 700 has been expanded and blood flow restored, the clinician retracts the clot treatment device 700 in a proximal direction, as shown in FIG. 8F. In one embodiment, the clot treatment device 700 and the delivery sheath 204 are pulled back simultaneously into the guide catheter 206, followed by the entire apparatus (i.e., clot treatment device 700, push member 202, delivery sheath 204 and guide catheter 206) being withdrawn through the heart and the venous circulation and out from the body.

Figure 9A:
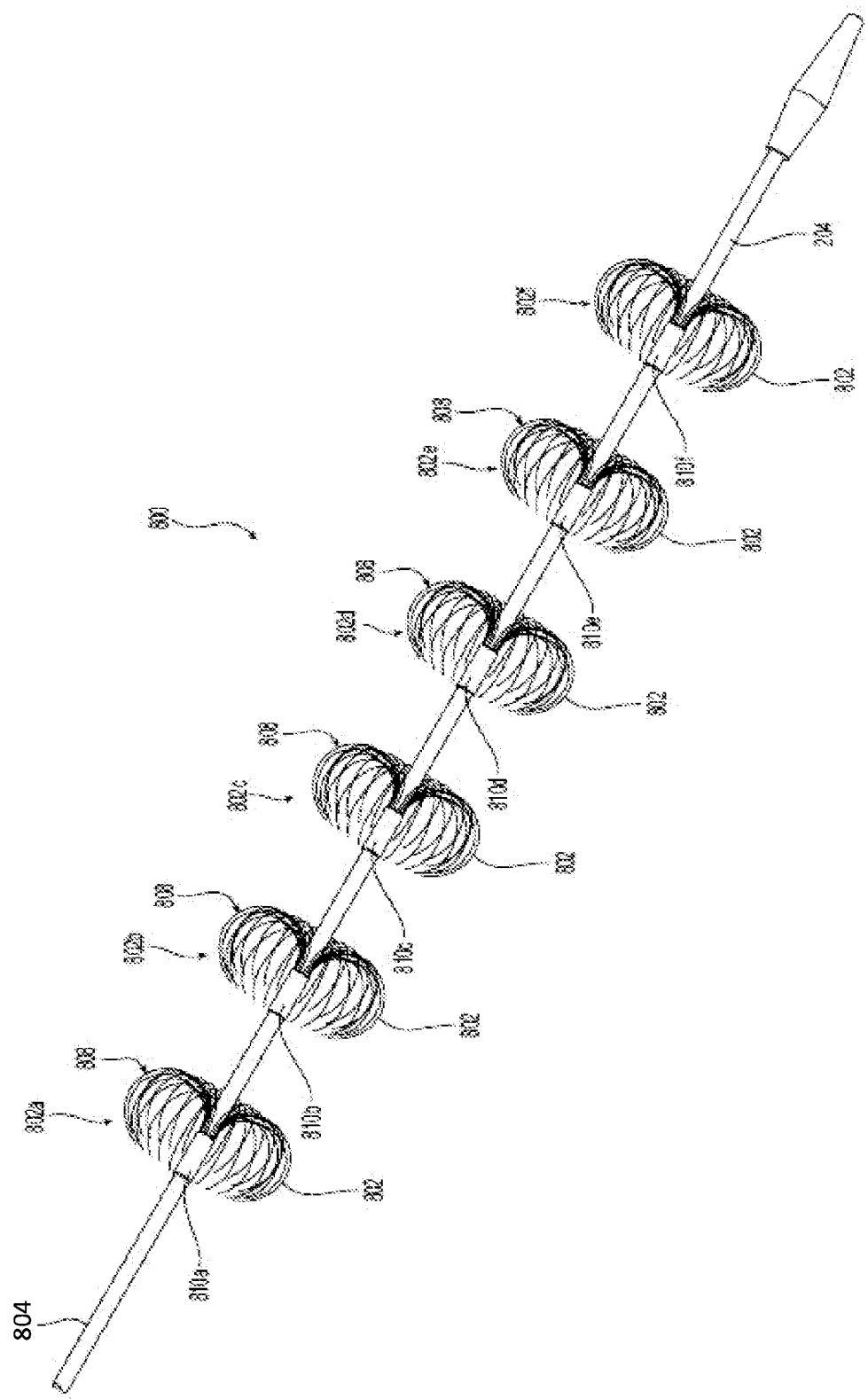
FIG. 9A is a perspective view of a clot treatment device configured in accordance with another embodiment of the present technology shown in a deployed state.
Figure 9B:
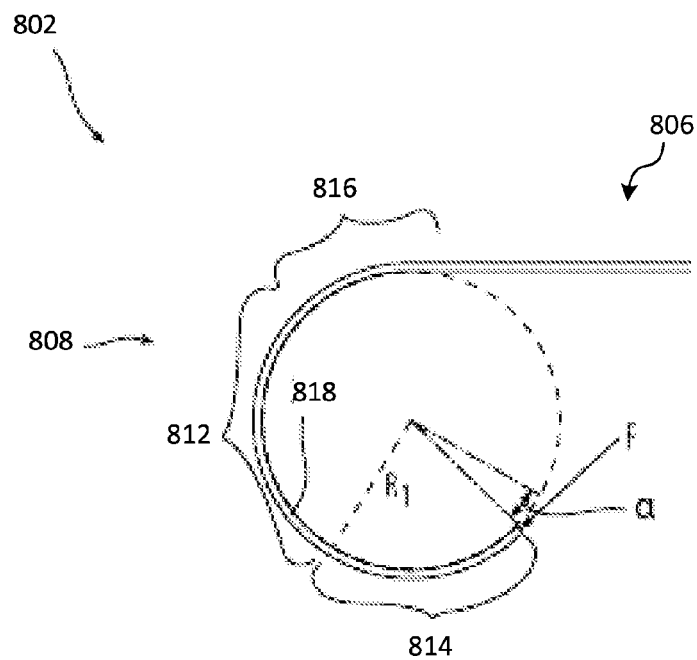
FIG. 9B is an isolated view of a clot engagement member configured in accordance with the present technology shown in a deployed state.

FIG. 9A is a perspective view of another embodiment of a clot treatment device 800 (also referred to herein as the "device 800") in an unrestricted expanded or deployed state that is well suited for removing clot material from a blood vessel (e.g., a pulmonary blood vessel). FIG. 9B is an enlarged, isolated side view of a clot engagement member 802 shown in FIG. 9A. Referring to FIGS. 9A-9B together, the device 800 can include a support member 804 and groups 802*a-f* of clot engagement members 202 spaced along the support member 804. Within each group 802*a-f*, individual clot engagement members 802 can be positioned about the circumference of the support member 804. Individual clot engagement members 802 can have a first portion 806 (FIG. 9B) coupled to the support member 804 by a hub 810 (labeled individually in FIG. 9A as 810*a-f*) and a second portion 808 extending distally from the first portion 806 and free to move relative to the support member 804. In the delivery state (not shown), the clot engagement members 802 can be generally linear and extend generally parallel to the support member 804. In the expanded state, as shown in FIGS. 9A-9B, the clot engagement members 802 can project radially outwardly relative to the support member 804 in a curved shape.

As best shown in FIG. 9B, the second portions 808 of the clot engagement members 802 can have a proximally facing section 812 which defines a proximally facing concave portion and, in some embodiments, the clot engagement members 802 can further include an end section 814 that curves radially inwardly from the proximally facing section 812. In a particular embodiment, a distal portion of the first portion 806 can extend distally of the corresponding hub 810*a-f*; however, in such embodiments, such distal portions of the clot engagement members 802 are relatively short (e.g., less than about 10 mm). When deployed within a blood vessel adjacent to clot material, the clot engagement members 802 are configured to penetrate the clot material along an arcuate path and hold clot material to the device 800, as discussed in greater detail below with reference to FIGS. 10A-10K.

In some embodiments, the groups 802*a-f* can be evenly spaced along the support member 804, and in other embodiments the groups 802*a-f* can have any spacing or state along the support member 804. Additionally, the arcuate clot engagement members 802 at one group (any of 802*a-f*) can have a different size than the arcuate clot engagement members 802 at a different group (any of 802*a-f*). The groups 802*a-f* can be deployed or expanded simultaneously (e.g., via a push-wire or other deployment methods) or consecutively (e.g., by retracting a sheath).

Figure 9C:
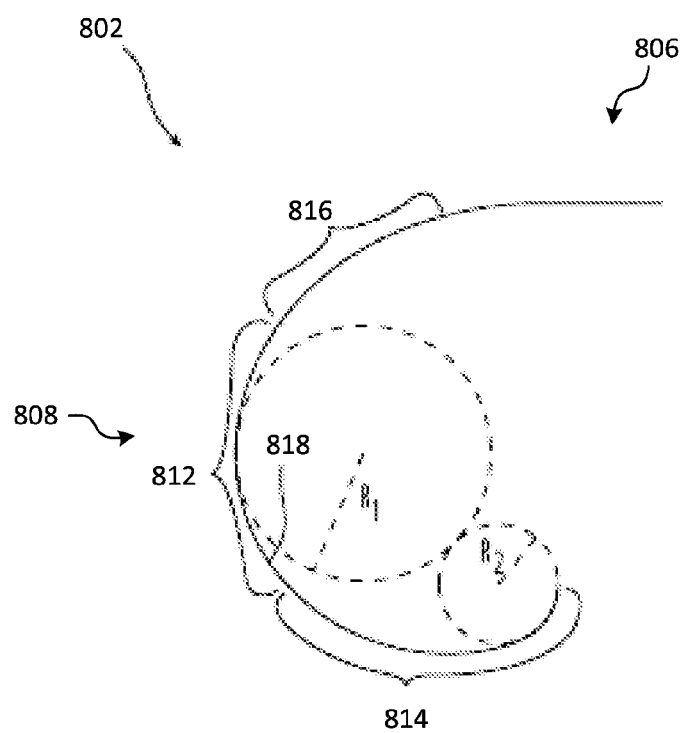
FIG. 9C is an isolated view of another embodiment of a clot engagement member configured in accordance with the present technology shown in a deployed state.

Individual clot engagement members 802 can be made from a shape memory material such that when the clot engagement members 802 are unconstrained, the clot engagement members 802 assume a preformed curved shape. As shown in FIG. 9B, the second portion 808 can have an arcuate shape that includes an outwardly extending section 816, the proximally facing section 812 extending from the outwardly extending section 816, and the end section 814 extending from the proximally facing section 812. In one embodiment, the demarcation between the proximally facing section 812 and the end section 814 occurs at an apex 818 of the second portion 808. The proximally facing section 812 is configured to retain clot material with the clot engagement member 802 as the device 800 is pulled proximally through the vessel (arrow P), and the apex 818 provides a smooth curve that can atraumatically slide along the vessel wall as the device 800 is pulled proximally through the vessel. In the embodiment shown in FIG. 9B, the second portion 808 of the clot treatment device 800 can have a single or constant radius of curvature $R_1$. In other embodiments, such as the clot engagement member 402 shown in FIG. 9C, the second portions 808 can have a plurality of radii of curvature, such as a first region with a first radius of curvature $R_1$ and a second region with a second radius of curvature $R_2$. In the embodiment shown in FIGS. 9A-9B, the second portions 808 of the clot engagement members 802 have a single radius of curvature that is the same for all of the clot engagement members 802 in all groups 802*a-f* and/or within a subset of groups 802*a-f*. In other embodiments, within the same group (any of 802*a-f*) or amongst groups 802*a-f*, the second portions 808 can have a constant radius of curvature and/or a plurality of radii of curvature (as shown in FIG. 9C). Moreover, in additional embodiments the device 800 can include a first group (any of 802a-f) of having second portions 808 with a first radius of curvature and a second group (any of 802a-f) having second portions 808 with a second radius of curvature different than the first radius of curvature. In some embodiments, the radius $R_1$ of the clot engagement members 802 can be between about 1.5 mm and about 12 mm, and in some embodiments, between about 2 mm and about 12 mm.

As shown in FIG. 9C, the arc length a of the clot engagement members 802 may be substantially greater than 180 degrees to provide several benefits in performance of clot engagement and retrieval. In particular, a greater arc length a can provide improved clot engagement during retraction when resistance due to clot friction and interference with the vessel wall deflects the clot engagement member 802 distally. A greater arc length a may provide more deflection and/or unravelling or straightening of the arcuate shape without loss of engagement with the clot. In some embodiments, the arc length a of the clot engagement members 802 can be greater than about 800 degrees. In some embodiments the arc length a of the clot engagement members 802 may be between about 800 degrees and 340 degrees and between about 240 degrees and 300 degrees in other embodiments. It can be advantageous to keep the arc length a under about 360 degrees so as to avoid overlap of the clot engagement member 802. Greater arc length a can allow for the use of smaller clot engagement member filaments or wires that may be particularly beneficial for minimization of the collapsed profile of the device. Greater arc length a can also allow for a larger total number of clot engagement members 802 that also enhance the ability of the device to remove embolic material from a vessel. Moreover, in some embodiments, the distal end of the clot engagement members 802 may define an angle with respect to the axis of the support member and/or the straight portion of the engagement members (as shown in FIG. 9C). This angle may be between about 30 degrees and about 90 degrees, and in some embodiments between about 40 degrees and about 80 degrees.

The clot engagement members 802 can be made from a variety of materials. In a particular embodiment, the clot engagement members 802 comprise a material with sufficient elasticity to allow for repeated collapse into an appropriately sized catheter and full deployment in a blood vessel. Such suitable metals can include nickel-titanium alloys (e.g., Nitinol), platinum, cobalt-chrome alloys, Elgiloy, stainless steel, tungsten, titanium and/or others. Polymers and metal/polymer composites can also be utilized in the construction of the clot engagement members. Polymer materials can include Dacron, polyester, polyethylene, polypropylene, nylon, Teflon, PTFE, ePTFE, TFE, PET, TPE, PLA silicone, polyurethane, polyethylene, ABS, polycarbonate, styrene, polyimide, PEBAX, Hytrel, polyvinyl chloride, HDPE, LDPE, PEEK, rubber, latex and the like. In some embodiments, the clot engagement members 802 may comprise an environmentally responsive material, also known as a smart material. Smart materials are designed materials that have one or more properties that can be significantly changed in a controlled fashion by external stimuli, such as stress, temperature, moisture, pH, electric or magnetic fields.

In some embodiments, portions of the exterior surfaces of the support member 804 and/or clot engagement members 802 may be textured, or the exterior surfaces can include microfeatures configured to facilitate engagement or adhesion of thrombus material (e.g., ridges, bumps, protrusions, grooves, cut-outs, recesses, serrations, etc.). In some embodiments, the clot engagement members 802 may be coated with one or more materials to promote platelet activation or adhesion of thrombus material. Adhesion of thrombi to clot engagement members 802 may facilitate capture and/or removal.

In some embodiments, the clot treatment device 800 can include between about 8 and about 80 clot engagement members 802, and in some embodiments, between about 12 and about 60 clot engagement members 802. In a particular embodiment, the clot treatment device 800 can include between about 16 and about 40 clot engagement members 802. The clot engagement members 802 can individually have one consistent diameter or have a variety of diameters (among the members 802) along their lengths. In addition, an individual clot engagement member 802 may have a tapered or varying diameter along its length to provide desired mechanical characteristics. The average diameter of the clot engagement members 802 can be between about 0.1 mm to about 0.2 mm in some embodiments and in a particular embodiment, between about 0.12 mm and 0.16 mm.

In any of the embodiments described herein, the clot engagement members 802 can be formed from a filament or wire having a circular cross-section. Additionally, the clot engagement members 802 can be formed from a filament or wire having a non-circular cross-section. For example, filaments or wires having square, rectangular and oval cross-sections may be used. In some embodiments, a rectangular wire (also known as a "flat wire") may have a height or radial dimension of between about 0.05 mm to about 0.2 mm. In some embodiments, a rectangular wire may have a width or transverse dimension of between about 0.08 mm to about 0.3 mm. In some embodiments, a rectangular wire may have a height to width ratio of between about 0.3 to about 0.9 and between about 1 and about 1.8.

Figure 10A:
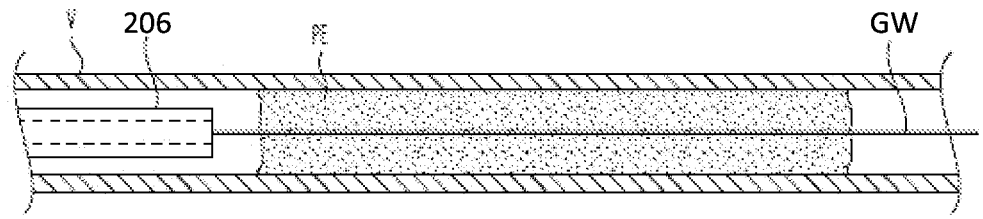
FIGS. 10A-10K illustrate a method for using the clot treatment device shown in FIG. 9A configured in accordance with the present technology to remove clot material from a vessel.
Figure 10B:
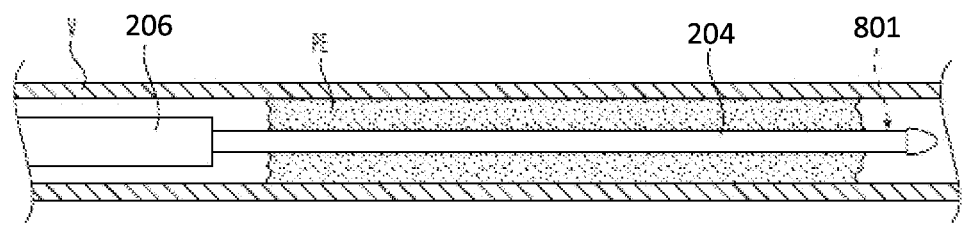
Figure 10C:
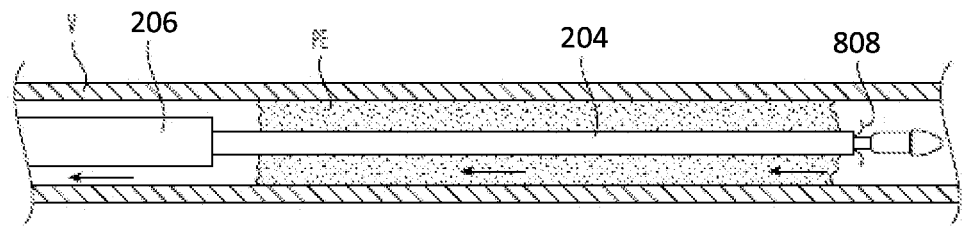
Figure 10D:
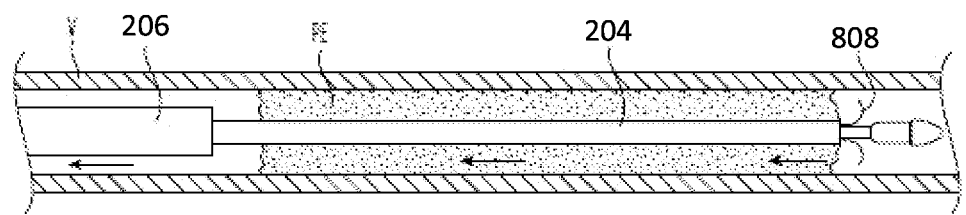
Figure 10E:
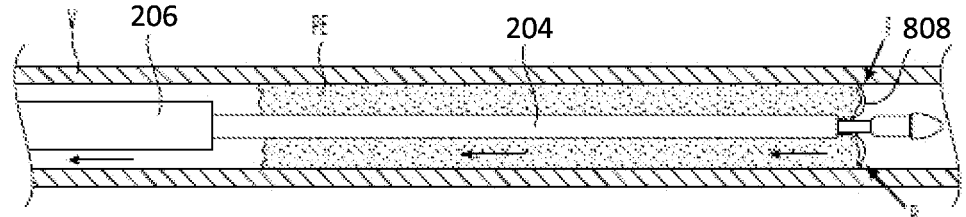

FIGS. 10A-10K illustrate one example for treating an embolism (e.g., a pulmonary embolism) with the clot treatment device 800 (and delivery system 910). FIG. 10A is a side view of a delivery system 910 positioned adjacent to an embolism or clot material PE within a pulmonary blood vessel V. As shown in FIG. 10A, the delivery sheath 204 containing the collapsed clot treatment device 800 (not shown) can be advanced together with the guide catheter 206 over the guidewire to the treatment site. For example, the guidewire can be inserted through the target pulmonary embolism PE. Referring to FIG. 10B, a distal portion of the guide catheter 206 and/or delivery sheath 204 can then be advanced through the pulmonary embolism PE such that the distal ends 801 of at least one group of the clot engagement members 802 are aligned with or positioned distal to a distal edge of the pulmonary embolism PE. In other embodiments (not shown), a distal portion of the guide catheter 206 and/or delivery sheath 204 can be positioned such that the distal ends 801 of at least one group of the clot engagement members 802 are positioned proximal to a distal edge of the pulmonary embolism PE.

Figure 10F:
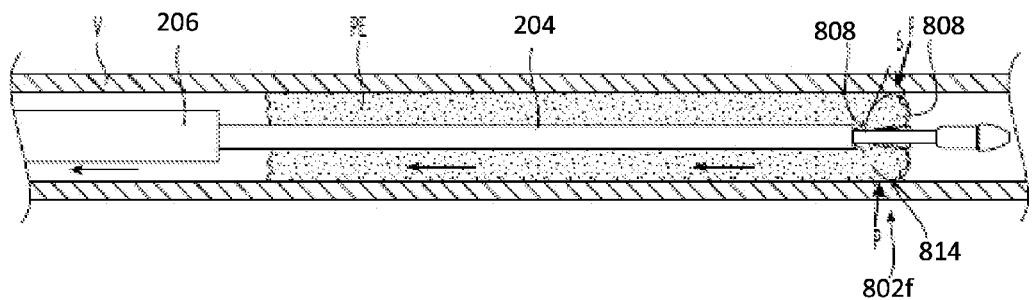

Once the device is positioned, the guidewire can then be removed proximally through a lumen of the delivery sheath 204 and/or guide catheter 206, and the delivery sheath 204 can be pulled proximally to a position proximal of the pulmonary embolism PE (as shown in FIG. 10B). As shown in FIGS. 10C-10G, the delivery sheath 204 can be retracted proximally to expose the distal portions of the second portions 808 of the clot engagement members such that the exposed portions radially expand and bend backwards in a proximal direction. As the second portions 808 expand, they extend into the pulmonary embolism PE around the device along an arcuate path P. The arcuate path P can extend radially outward and proximally with respect to the support member (not shown) and, as shown in FIG. 10F, can eventually curve radially inwardly. The second portions 808 can thus form hook-like capture elements that penetrate into and hold clot material to the device 800 for subsequent removal. Moreover, should the second portions 808 extend radially outwardly enough to touch the vessel wall, the end sections 814 of the second portions 808 form an atraumatic surface that can abut or apply pressure to the vessel wall without damaging the vessel wall. In some embodiments, the device presents a plurality of arcuate members that may be substantially parallel with the axis of the device at the point of contact with the vessel wall when in the deployed state.

Figure 10G:
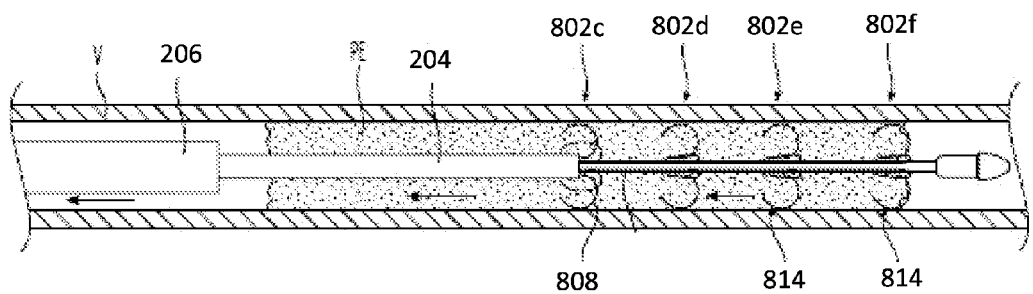
Figure 10H:
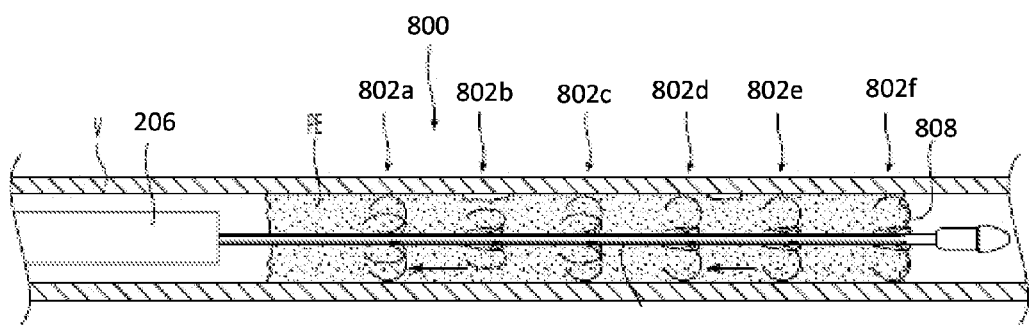
Figure 10I:
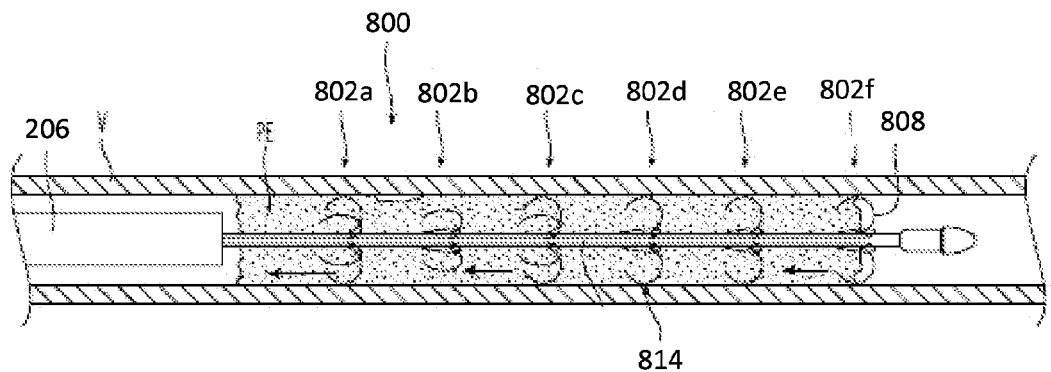
Figure 10J:
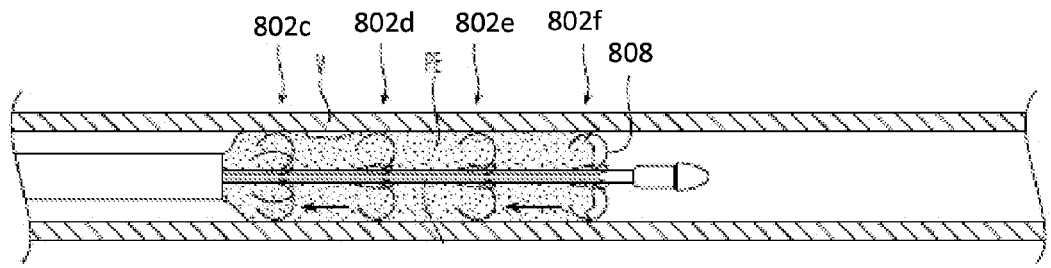
Figure 10K:
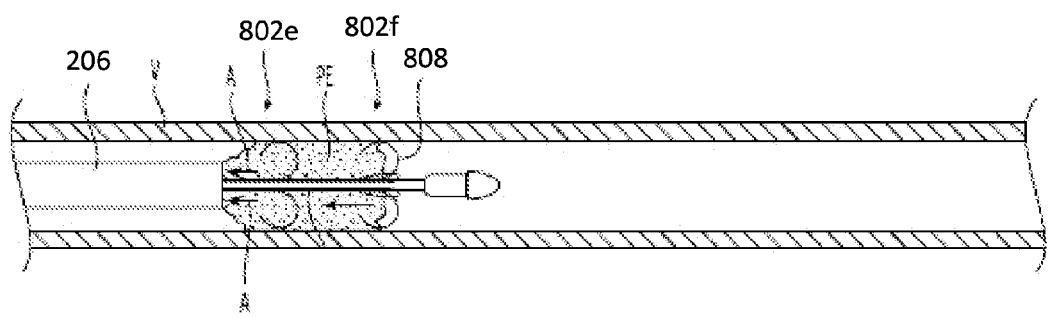

In some embodiments, the delivery sheath 204 can be withdrawn so as to expose only a portion of the clot engagement members. Additionally, in those embodiments having two or more groups of clot engagement members, the delivery sheath 204 can be withdrawn to expose all or some of the groups of clot engagement members. As shown in FIG. 10G, the delivery sheath 204 can continue to be withdrawn proximally to expose additional second portions 808 and/or groups of clot engagement members 802a-f. Clot engagement members 802a-f may just contact or be slightly deflected by the vessel wall. If the device is sized such that the diameter of the clot engagement members are larger than the vessel diameter (e.g., "over-sized"), the clot engagement members may be compressed by the vessel wall. Thus, while fully deployed, the device may be in state of a small amount of radial compression. In some embodiments, the device may be diametrically over-sized by between about 5% and 50% and in other embodiments between about 10% and 25%.

As shown in FIGS. 10H-10K, once at least a portion of the clot engagement members and/or second portions 808 have penetrated and engaged the targeted clot material PE, the clot treatment device 800 can be withdrawn proximally, thereby pulling at least a portion of the clot material PE in a proximal direction with the device 800. For example, the push member 202 and delivery sheath 204 can be retracted proximally at the same time and rate. As such, the guide catheter 206 can be held in place while the delivery sheath 204, clot material PE, and clot treatment device 800 are pulled proximally into the guide catheter 206. The curved shape of the second portions 808 increases the surface area of the clot engagement members 802 in contact with the clot material PE, thus increasing the proximal forces exerted on the clot material. Withdrawal of the device 800 not only removes the clot but also can increase blood flow through the vessel.

In some embodiments, the catheter system 200 and/or ID can be a device commonly known as a "stent retriever." Exemplary stent retrievers that may be utilized with the RA system 1000 and/or RA device 100 include the Trevo XP ProVue Retriever, commercially available from Stryker Neurovascular (Freemont, Calif.), the Solitaire FR revascularization device, commercially available from Medtronic Covidien (Dublin, Ireland) and the Revive SE clot removal device, commercially available in Europe from Johnson and Johnson Codman Neuro (Raynham, Mass.). The devices typically comprise a self-expanding, fenestrated framework or mesh. Exemplary designs are shown in U.S. Pat. No. 8,795,317 to Grandfield et al., U.S. Pat. No. 8,940,003 to Slee et al., and U.S. Pat. No. 8,679,142 to Slee et al., all of which are incorporated herein by reference in their entireties. For example, in some embodiments, the stent retriever can comprise a self-expandable mesh structure comprising a first plurality of mesh cells. In some embodiments, the stent retriever is reversibly self-expandable, and in a particular embodiment, the stent retriever is fully retrievable or retractable. The mesh structure can have a proximal portion, a distal portion, and a tapering portion comprising a second plurality of mesh cells. The tapering portion can be disposed toward the proximal portion of the mesh structure. The tapering portion can converge at a connection point located at a proximal end of the tapering portion. The mesh structure can be pre-formed to assume a volume-enlarged form and, in the volume-enlarged form, take the form of a longitudinally open tube tapering toward the connection point.

Additional embodiments of clot treatment devices for use with the RA device 100 and/or RA system 1000 are described in U.S. patent application Ser. No. 14/299,933, filed Jun. 9, 2014, U.S. patent application Ser. No. 14/299,997, filed Jun. 9, 2014, U.S. patent application Ser. No. 13/843,742, filed Mar. 15, 2013, and U.S. patent application Ser. No. 14/288,778, filed May 28, 2014, all of which are incorporated herein by reference in their entireties. In some embodiments, the RA system 1000 and/or RA device 100 may be combined with a catheter and a clot treatment device that is configured to treat an embolus in the cerebrovasculature or acute stroke.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

I claim:

1. An apparatus for use with a catheter system, wherein the catheter system enables intravascular delivery of an interventional device to a treatment site in a blood vessel, the apparatus comprising:
   a housing configured to be releasably coupled to a proximal portion of the catheter system;
   an actuation mechanism coupled to the housing, wherein the actuation mechanism includes—
     a lever movably coupled to the housing;
     a locking portion configured to engage a portion of the catheter system;
   a pressure source coupled to the housing and the actuation mechanism; and
   wherein movement of the lever simultaneously—
     activates the pressure source to generate pressure, and
     retracts at least a portion of the catheter system.

2. The apparatus of claim 1 wherein the pressure source is configured to be manually operated.

3. The apparatus of claim 2 wherein the pressure source is a syringe.

4. The apparatus of claim 1 wherein the pressure source is an automatic pressure source that is configured to intermittently generate negative pressure.

5. The apparatus of claim 1 wherein the blood vessel is a pulmonary artery.

6. The apparatus of claim 1 wherein the blood vessel is a cerebral blood vessel.

7. The apparatus of claim 1 wherein the pressure source is a mechanical or electrical pump.

8. A system for extracting thrombus from a blood vessel of a human patient, the system comprising:
   a catheter including— a first elongated shaft having proximal portion and a distal portion, wherein an inner surface of the first elongated shaft defines a lumen, a second elongated shaft positioned at least partially within the lumen of the first elongated shaft, wherein the second elongated shaft has a proximal portion and a distal portion, and a treatment device coupled to the distal portion of the second elongated shaft;

a pressure source;

a retraction and aspiration device including an actuation mechanism configured to be coupled to the pressure source and at least one of the first and/or second elongated shafts, wherein the actuation mechanism includes a lever; and wherein movement of the lever simultaneously generates a negative pressure in the lumen and retracts the second elongated shaft.

9. The system of claim 8 wherein:

the treatment device comprises an expandable braided structure having a delivery state and a deployed state, when the treatment device is in the deployed state, the treatment device includes a plurality of radially extending portions and at least one cylindrical portion, wherein the cylindrical portion is between a pair of the radially extending portions, and wherein the treatment device is configured to be delivered to a treatment site within a pulmonary blood vessel to remove clot material from the treatment site.

10. The system of claim 8 wherein:

the treatment device comprises an expandable braided structure having a delivery state and a deployed state, when the treatment device is in the deployed state, the treatment device includes a plurality of radially extending portions and at least one cylindrical portion, wherein the cylindrical portion is between a pair of the radially extending portions, and wherein the treatment device is configured to be delivered to a treatment site within a cerebral blood vessel to remove clot material from the treatment site.

11. The system of claim 8 wherein the treatment device comprises:

a support member;

a first plurality of arcuate clot engagement members configured to deploy at a first location along the support member;

a second plurality of arcuate clot engagement members configured to deploy at a second location along the support member proximal of the first location;

wherein, when in the deployed state, the individual clot engagement members of the first and second pluralities of clot engagement members extend radially outward, then proximally with respect to the support member, then curve radially inwardly;

wherein the treatment device is configured to be delivered to a treatment site within a pulmonary blood vessel to remove clot material from the treatment site.

12. The system of claim 8 wherein the treatment device comprises:

a support member;

a first plurality of arcuate clot engagement members configured to deploy at a first location along the support member;

a second plurality of arcuate clot engagement members configured to deploy at a second location along the support member proximal of the first location;

wherein, when in the deployed state, the individual clot engagement members of the first and second pluralities of clot engagement members extend radially outward, then proximally with respect to the support member, then curve radially inwardly;

wherein the treatment device is configured to be delivered to a treatment site within a cerebral blood vessel to remove clot material from the treatment site.

13. The system of claim 8 wherein the pressure source is configured to be manually operated.

14. The system of claim 8 wherein the pressure source is an automatic pressure source that is configured to intermittently generate negative pressure.

15. A method for the intravascular treatment of clot material from a treatment site within a blood vessel of a human patient, the method comprising:

providing a retraction and aspiration device having an actuation mechanism, wherein the actuation mechanism has an actuator and is configured to be coupled to a pressure source and a proximal portion of a catheter, wherein the catheter includes an elongated shaft configured to be intravascularly positioned at the treatment site and an elongated member positioned within a lumen of the elongated shaft, wherein a distal portion of the elongated member includes a treatment device; and moving the actuator to simultaneously generate a negative pressure within the lumen of the elongated shaft via the pressure source and retract the elongated member; and incrementally drawing the treatment device and the clot material into the lumen of the elongated shaft.

16. The method of claim 15 wherein the actuator is a lever coupled to the retraction and aspiration device.

17. The method of claim 15 further comprising continuing to draw the clot material into the lumen of the elongated shaft when a distal terminus of the treatment device is spaced proximally from a distal terminus of the elongated shaft.

18. The method of claim 15 wherein activating the actuation mechanism occurs at a first time and wherein the method further comprises activating the actuation mechanism at a second time, and wherein the method further comprises:

removing between 10 cc and 80 cc of fluid from the treatment site during the first activation of the actuation mechanism; and removing between 10 cc and 80 cc of fluid from the treatment site during the second activation of the actuation mechanism.

19. The method of claim 15 wherein the treatment device comprises an expandable braided structure having a delivery state and a deployed state, wherein, when the treatment device is in the deployed state, the treatment device includes a plurality of radially extending portions and at least one cylindrical portion, wherein the cylindrical portion is between a pair of the radially extending portions.

20. The method of claim 15 wherein the treatment device comprises:

a support member;

a first plurality of arcuate clot engagement members configured to deploy at a first location along the support member;

a second plurality of arcuate clot engagement members configured to deploy at a second location along the support member proximal of the first location; and wherein, when in the deployed state, the individual clot engagement members of the first and second pluralities of clot engagement members extend radially outward, then proximally with respect to the support member, then curve radially inwardly.

21. The method of claim 15 wherein the treatment device is a stent retriever.

22. The method of claim 15 wherein the pressure source is one of a syringe, a mechanical pump, or an electrical pump.

23. A method for the intravascular treatment of clot material from a treatment site within a cerebral vessel of a human patient, the method comprising:
provimding a retraction and aspiration device having an actuation mechanism, wherein the actuation mechanism is configured to be coupled to a pressure source and a proximal portion of a catheter, wherein the catheter includes an elongated shaft configured to be intravascularly positioned at the treatment site and an elongated member positioned within a lumen of the elongated shaft, wherein a distal portion of the elongated member includes a treatment device; and
activating an actuation mechanism to generate a negative pressure within the lumen of the elongated shaft via the pressure source and retract the elongated member; and
incrementally drawing the treatment device and the clot material into the lumen of the elongated shaft.

24. The method of claim 23 wherein activating an actuation mechanism includes moving a lever coupled to the retraction and aspiration device.

25. The method of claim 23 further comprising continuing to draw the clot material into the lumen of the elongated shaft when a distal terminus of the treatment device is spaced proximally from a distal terminus of the elongated shaft.

26. The method of claim 23 wherein activating the actuation mechanism occurs at a first time and wherein the method further comprises activating the actuation mechanism at a second time, and wherein the method further comprises:
removing between 20 cc and 80 cc of fluid from the treatment site during the first activation of the actuation mechanism; and
removing between 20 cc and 80 cc of fluid from the treatment site during the second activation of the actuation mechanism.

27. The method of claim 23 wherein the treatment device comprises an expandable braided structure having a delivery state and a deployed state, wherein, when the treatment device is in the deployed state, the treatment device includes a plurality of radially extending portions and at least one cylindrical portion, wherein the cylindrical portion is between a pair of the radially extending portions.

28. The method of claim 23 wherein the treatment device comprises:
a support member;
a first plurality of arcuate clot engagement members configured to deploy at a first location along the support member;
a second plurality of arcuate clot engagement members configured to deploy at a second location along the support member proximal of the first location; and
wherein, when in the deployed state, the individual clot engagement members of the first and second pluralities of clot engagement members extend radially outward, then proximally with respect to the support member, then curve radially inwardly.

29. The method of claim 23 wherein the treatment device is a stent retriever.

30. The apparatus of claim 23 wherein the pressure source is one of a syringe, a mechanical pump, or an electrical pump.

* * * * *

UNITED STATES PATENT AND TRADEMARK OFFICE
CERTIFICATE OF CORRECTION

PATENT NO. : 9,526,865 B2
APPLICATION NO. : 14/834793
DATED : December 27, 2016
INVENTOR(S) : Richard Quick It is certified that error appears in the above-identified patent and that said Letters Patent is hereby corrected as shown below:

On the page 3, in Column 2, under "Other Publications", Line 65, delete "Neurolntervent" and insert -- NeuroIntervent --, therefor.

In Column 15, Line 33, delete "severe." and insert -- severe, --, therefor.

In Column 22, Line 10, in Claim 13, before "configured" delete "a".

In Column 23, Line 10, in Claim 23, before "vessel" insert -- blood --.

In Column 24, Line 32, in Claim 30, delete "apparatus" and insert -- method --.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*